United States Patent
Inoue

(10) Patent No.: US 8,169,618 B2
(45) Date of Patent: May 1, 2012

(54) OPTICAL STRUCTURE MEASURING APPARATUS AND OPTICAL PROBE THEREOF

(75) Inventor: Toshiyuki Inoue, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 176 days.

(21) Appl. No.: 12/779,540

(22) Filed: May 13, 2010

(65) Prior Publication Data

US 2010/0290059 A1 Nov. 18, 2010

(30) Foreign Application Priority Data

May 14, 2009 (JP) ................. 2009-117655

(51) Int. Cl.
 G01B 9/02 (2006.01)
 G01B 11/02 (2006.01)
(52) U.S. Cl. ...................... 356/479; 356/497
(58) Field of Classification Search .......... 356/479, 356/497
 See application file for complete search history.

(56) References Cited

U.S. PATENT DOCUMENTS

| | | | |
|---|---|---|---|
| 6,788,861 B1 | 9/2004 | Utsui et al. | |
| 7,242,833 B2 | 7/2007 | Yang et al. | |
| 7,511,822 B2* | 3/2009 | Fujita | 356/479 |
| 7,692,797 B2* | 4/2010 | Kawahara | 356/497 |
| 7,701,585 B2* | 4/2010 | Hatori | 356/479 |
| 7,705,992 B2* | 4/2010 | Hatori et al. | 356/479 |
| 7,751,056 B2* | 7/2010 | Teramura | 356/477 |
| 2007/0115477 A1* | 5/2007 | Teramura et al. | 356/479 |
| 2007/0159637 A1* | 7/2007 | Toida | 356/456 |
| 2007/0159639 A1* | 7/2007 | Teramura et al. | 356/485 |
| 2007/0211255 A1* | 9/2007 | Ohkubo | 356/479 |
| 2008/0117427 A1 | 5/2008 | Teramura et al. | |
| 2008/0117431 A1* | 5/2008 | Teramura | 356/511 |
| 2009/0213387 A1* | 8/2009 | Nakabayashi et al. | 356/496 |
| 2009/0279098 A1* | 11/2009 | Ohbayashi et al. | 356/478 |
| 2010/0290059 A1* | 11/2010 | Inoue | 356/477 |
| 2011/0181889 A1* | 7/2011 | Kabetani et al. | 356/496 |
| 2011/0267583 A1* | 11/2011 | Hayashi | 351/206 |

FOREIGN PATENT DOCUMENTS

| | | |
|---|---|---|
| JP | 2001-051225 A | 2/2001 |
| JP | 2004-502957 A | 1/2004 |
| JP | 2008-128708 A | 6/2008 |

* cited by examiner

*Primary Examiner* — Patrick J Connolly
(74) *Attorney, Agent, or Firm* — Sughrue Mion, PLLC

(57) ABSTRACT

In an embodiment of the present invention, an OCT probe is configured by including: a thin and long substantially cylindrical sheath whose distal end is closed; an n-reflecting surface body, as an irradiating device, which has n reflecting surfaces (with n being an integer of three or more) and which is provided in a distal end portion of the sheath; a torque transmitting coil, as a rotating device, which is provided along the longitudinal axis of the sheath and which transmits rotational torque for rotating each of the reflection surfaces of the n-reflecting surface body about the longitudinal axis of the sheath; and n fibers (1) to (n), as an n-channel waveguide device, which are provided and fixed in the sheath in a side by side relationship with the torque transmitting coil.

22 Claims, 16 Drawing Sheets

OPTICAL STRUCTURE MEASURING APPARATUS AND OPTICAL PROBE THEREOF

BACKGROUND OF THE INVENTION

1. Field of the Invention

The present invention relates to an optical structure measuring apparatus and an optical probe thereof, and more particularly to an optical structure measuring apparatus and an optical probe thereof, that are featured in a radial scanning method in which measuring light beams are radially scanned across an object to be measured by the measuring light beams.

2. Description of the Related Art

Conventionally, when an optical tomographic image of a living tissue is obtained, an optical tomographic image obtaining apparatus utilizing the OCT (Optical Coherence Tomography) measurement may be used. The optical tomographic image obtaining apparatus divides a low coherent light beam emitted from a light source into a measuring light beam and a reference light beam. Thereafter, the optical tomographic image obtaining apparatus multiplexes, with the reference light beam, a light beam reflected or back-scattered by a measuring object at the time of irradiating the measuring light beam onto the measuring object, and obtains an optical tomographic image on the basis of the intensity of the interference light beam of the reflected light beam and the reference light beam (Japanese Patent Application Laid-Open No. 2008-128708).

The above-described OCT measurement is roughly divided into two kinds: the TD-OCT (Time domain OCT) measurement and the FD-OCT (Fourier Domain OCT) measurement.

The TD-OCT measurement is a method in which a reflected light beam intensity distribution corresponding to a depth direction position (hereinafter referred to as depth position) of a measuring object is obtained by measuring the intensity of the interference light beam while changing the optical path length of the reference light beam.

On the other hand, the FD-OCT measurement is a method in which the intensity of the interference light beam is measured for each spectral component of the light beam without changing the optical path of the reference light beam and the signal light beam, and in which the frequency analysis (as represented by the Fourier transform) of the spectral interference intensity signals obtained by the measurement is performed by a computer so that a reflected light beam intensity distribution corresponding to a depth position is obtained. In recent years, the FD-OCT measurement has been attracting attention as a method which does not need the mechanical scanning necessary for the TD-OCT measurement, and which can perform the measurement at high speed.

As shown in FIG. 16, an OCT probe 800 used for the conventional OCT measurement acquires a return light beam L3 in such a manner that an optical fiber FB1 and a torque transmitting coil 824, which are provided on the rotation side, are rotated by an optical rotary joint (not shown) in the arrow R direction in FIG. 16, and that a measuring light beam L1 emitted from an optical lens 828 is thereby irradiated onto a measuring object S while the radial scanning is performed along the arrow R direction.

Thereby, over the entire circumference in the circumferential direction of a sheath 820 of the OCT probe 800, it is possible to accurately capture desired portions of the measuring object S and possible to obtain the return light beam L3 reflected by the measuring object S.

Further, when a plurality of pieces of optical structure information are obtained in order to generate an optical three-dimensional structure image, the optical lens 828 is moved by an axial movement driving section to an end of the region in which the optical lens 828 can be moved in the arrow S1 direction. Then, the optical lens 828 is moved in the S2 direction by each predetermined amount while optical structure information of the tomogram is acquired, or is moved to the end of the movable region while the acquisition of the optical structure information and the movement by the predetermined amount in the S2 direction are alternately repeated.

In this way, the plurality of pieces of optical structure information of the desired range of the measuring object S are obtained, so that an optical three-dimensional structure image can be obtained on the basis of the acquired plurality of pieces of optical structure information.

That is, while the optical structure information in the depth direction (first direction) of the measuring object S is acquired on the basis of the interference signal, the radial scanning of the measuring object S is performed in the arrow R direction (circumferential direction of the sheath 820) in FIG. 16. Thereby, it is possible to obtain the optical structure information on the scanning surface which is formed by the depth direction (first direction) of the measuring object S and the direction (second direction) substantially orthogonal to the depth direction. Further, a plurality of pieces of optical structure information used for generating an optical three-dimensional structure image can be obtained by moving the scanning surface along the direction (third direction) substantially orthogonal to the scanning surface.

On the other hand, an OCT probe is disclosed, for example, in Japanese National Publication of International Patent Application No. 2004-502957, in which a plurality of light beams emitted from a plurality of optical fibers are simultaneously scanned along the optical axis by arranging the plurality of optical fibers and an optical path converging device so as to allow the focal points of the light beams to be formed at continuous positions, and in which the continuous focal points are scanned by a mirror in the lateral direction with respect to the optical axis so that the continuous focal points can be scanned over a two-dimensional region.

Further, an OCT probe is disclosed, for example, in Japanese Patent Application Laid-Open No. 2001-51225, in which a light beam emitted from an optical fiber is irradiated onto a measuring object by using a polygon mirror having a plurality of reflecting surfaces with mutually different reflection angles, and in which a predetermined two-dimensional region can be obtained at high speed by rotating the polygon mirror.

SUMMARY OF THE INVENTION

However, the conventional OCT probe 800 described with reference to FIG. 16 has a problem that when the radial scanning is performed over the entire circumference of the sheath, the optical lens 828 needs to be driven and rotated together with the rotation side optical fiber FB1, and that the acquisition time of the optical structure information over the entire circumference is restricted by the rotation speed of the optical lens 828 and the rotation side optical fiber FB1 so as to limit the increase in the acquisition speed of the optical structure information. Also in the scanning principle of the OCT probe disclosed in National Publication of International Patent Application No. 2004-502957, the acquisition time of the optical structure information over the entire circumference is restricted by the rotation speed of the mirror.

Further, since the conventional OCT probe 800, as described with reference to FIG. 16, is configured by making an optical fiber and an optical system (prism or hemispherical lens) included and fixed in the torque transmitting coil, and since the optical fiber also needs to be rotated according to the rotation of the torque transmitting coil, an optical rotary joint is needed as a component for optical transmission. The insertion of the component causes a light quantity loss of the measuring light beam guided to the measuring object S, and a reflection loss in the component, or a light quantity loss of the light beam reflected by the measuring object S. This also results in a problem of adverse influence on the image quality, such as a problem of deterioration of the S/N ratio.

On the other hand, in the scanning principle of the OCT probe disclosed in Japanese Patent Application Laid-Open No. 2001-51225, since the two dimensional scanning is performed by rotating the polygon mirror, the scanning range of the two-dimensional scanning is limited, so that the radial scanning cannot be performed over the entire circumference of the sheath.

The present invention has been made in view of the above described circumstances. An object of the present invention is to provide an optical structure measuring apparatus and its optical probe which are capable of performing, at high speed, the radial scanning for acquiring optical structure information of a measuring object, and which are capable of improving the S/N ratio.

To this end, an optical structure measuring apparatus according to a first aspect of the present invention includes: an optical probe having a thin and long sheath whose distal end is closed, an n-channel waveguide device in which n is an integer of three or more and which is inserted and fixed in the sheath along the longitudinal axis of the sheath so as to guide optical light beams, an irradiating device which is provided in a distal end portion of the sheath and which deflects a light beam emitted from each of the channels of the n-channel waveguide device in a radial direction about the longitudinal axis of the sheath to irradiate a measuring object with the deflected light beam, a rotating device which rotates the irradiating device about the longitudinal axis, and a forward/backward moving device which moves the n-channel waveguide device and the irradiating device forward and backward in the direction along the longitudinal axis; a light source device which emits a light beam having wavelengths in a wide band; a branching device which branches the light beam from the light source device into a measuring light beam and a reference light beam; a branching and light guiding device which branches the measuring light beam in correspondence with each of the channels of the n-channel waveguide device to allow the branched light beam to be guided by each of the channels of the n-channel waveguide device; an n-channel interference light detecting device which detects an interference light beam obtained, for each of the channels of the n-channel waveguide device, by making the reference light beam interfere with a return light beam as the measuring light beam which is returned from the measuring object by being guided by each of the channels of the n-channel waveguide device via the branching and light guiding device; an n-channel interference signal generating device which generates an interference signal representing a signal intensity in the depth direction of the measuring object, on the basis of each of the interference light beams detected by the n-channel interference light detecting device; and a tomographic structure image generating device which generates a tomographic structure image of the measuring object on the basis of each of the interference signals generated by the re-channel interference signal generating device.

In the optical structure measuring apparatus according to the first aspect of the present invention, the radial scanning for acquiring optical structure information of the measuring object can be performed at high speed and the S/N ratio can be improved in such a manner that the optical probe is configured such that the n-channel wave guide device, in which n is an integer of three or more, is inserted and fixed in the sheath along the longitudinal axis of the sheath so as to guide light beams, such that the irradiating device deflects the light beam emitted from each of the channels of the n-channel waveguide device in a radial direction about the longitudinal axis of the sheath, so as to irradiate a measuring object with the deflected light beam, such that the rotating device rotates the irradiating device about the longitudinal axis, and such that the forward/backward moving device moves the n-channel waveguide device and the irradiating device forward and backward in the direction along the longitudinal axis, and in such a manner that the branching device branches a light beam from the light source device to a measuring light beam and a reference light beam, that the branching and light guiding device branches the measuring light beam in correspondence with each of the channels of the n-channel waveguide device to allow the branched light beam to be guided by each of the channels of the n-channel waveguide device, that the n-channel interference light detecting device detects an interference light beam obtained, for each of the channels of the n-channel waveguide device, by making the reference light beam interfere with a return light beam as the measuring light beam which is returned from the measuring object by being guided by each of the channels of the n-channel waveguide device via the branching and light guiding device; that the n-channel interference signal generating device generates an interference signal representing a signal intensity in the depth direction of the measuring object, on the basis of each of the interference light beams detected by the n-channel interference light detecting device; and that the tomographic structure image generating device generates a tomographic structure image of the measuring object on the basis of each of the interference signals generated by the n-channel interference signal generating device.

An optical structure measuring apparatus according to a second aspect of the present invention is preferably such that in the optical structure measuring apparatus according to the first aspect, the irradiating device is configured by an n-surface light deflecting and irradiating device which has a substantially n-sided pyramid shape formed in such a manner that a vertex side of an n-sided pyramid having a planar n-sided polygon shaped bottom surface is cut at a predetermined height from the bottom surface, and which has n light deflecting surfaces that are formed by the side surfaces of the substantially n-sided pyramid, and that are arranged to be rotatable about the longitudinal axis.

An optical structure measuring apparatus according to a third aspect of the present invention is preferably such that, in the optical structure measuring apparatus according to the second aspect, the planar n-sided polygon shape is formed into a rotationally symmetrical shape about the longitudinal axis.

An optical structure measuring apparatus according to a fourth aspect of the present invention is preferably such that in the optical structure measuring apparatus according to one of the first to third aspects, the rotating device is configured by a torque transmitting coil, a distal end of which is integrally connected to the rotation center of the n-surface light deflecting and irradiating device, and which is rotatably inserted in the sheath along the longitudinal axis of the sheath, and a motor, a rotary shaft of which is connected to the proximal end of the torque transmitting coil, and which rotates the torque transmitting coil about the longitudinal axis.

An optical structure measuring apparatus according to a fifth aspect of the present invention is preferably such that in the optical structure measuring apparatus according to one of the first to third aspects, the rotating device is configured by a motor which is provided in the sheath on the distal end side from the n-surface light deflecting and irradiating device, and which uses, as its rotary shaft, the longitudinal axis integrally connected to the rotation center of the n-surface light deflecting and irradiating device.

An optical structure measuring apparatus according to a sixth aspect of the present invention is preferably such that in the optical structure measuring apparatus according to one of the first to fifth aspects, the branching device is configured by an re-channel branching device each channel of which is provided for each of the channels of the n-channel interference light detecting device.

An optical structure measuring apparatus according to a seventh aspect of the present invention preferably further includes, in the optical structure measuring apparatus according to one of the first to fifth aspects, an n-channel reference light branching device that branches the reference light beam into channel reference light beams each of which corresponds to each of the channels of the n-channel interference light detecting device, and each of which is made to interfere with each return light beam as the measuring light beam that is guided from the measuring object by each of the channels of the n-channel waveguide device via the branching and light guiding device.

An optical structure measuring apparatus according to an eighth aspect of the present invention preferably further includes, in the optical structure measuring apparatus according to one of the first to sixth aspects, an optical path length correcting device which corrects the optical path length of the reference light beam.

An optical structure measuring apparatus according to a ninth aspect of the present invention preferably further includes, in the optical structure measuring apparatus according to the seventh aspect, n or n−1 channel optical path length correcting devices, each of which is provided for each of the channels of the n-channel interference light detecting device, so as to correct the optical path length of the channel reference light beam.

An optical structure measuring apparatus according to a tenth aspect of the present invention is preferably such that in the optical structure measuring apparatus according to one of the first to ninth aspects, the light source device is configured by n or less light sources each of which emits the light beam having wavelengths in the wide band.

An optical structure measuring apparatus according to an eleventh aspect of the present invention preferably further includes, in the optical structure measuring apparatus according to the first to tenth aspect, a three-dimensional structure image generating device which generates a three-dimensional structure image of the measuring object on the basis of the plurality of tomographic structure images taken along the longitudinal axis.

In the optical structure measuring apparatus according to the twelfth aspect of the present invention, the radial scanning for acquiring optical structure information of the measuring object can be performed at high speed and the S/N ratio can be improved in such a manner that the optical probe is configured such that the n-channel wave guide device, in which n is an integer of two or more, is inserted and fixed in the sheath along the longitudinal axis of the sheath so as to guide light beams, such that the irradiating device deflects the light beam emitted from each of the channels of the n-channel waveguide device in a radial direction about the longitudinal axis of the sheath, so as to irradiate a measuring object with the deflected light beam, such that the rotating device rotates the irradiating device about the longitudinal axis, and such that the forward/backward moving device moves the n-channel waveguide device and the irradiating device forward and backward in the direction along the longitudinal axis, and in such a manner that the branching device branches a light beam from the light source device to a measuring light beam and a reference light beam, that the branching and light guiding device branches the measuring light beam in correspondence with each of the channels of the n-channel waveguide device to allow the branched light beam to be guided by each of the channels of the n-channel waveguide device, that the n-channel interference light detecting device detects an interference light beam obtained, for each of the channels of the n-channel waveguide device, by making the reference light beam interfere with a return light beam as the measuring light beam which is returned from the measuring object by being guided by each of the channels of the n-channel waveguide device via the branching and light guiding device; that the n-channel interference signal generating device generates an interference signal representing a signal intensity in the depth direction of the measuring object, on the basis of each of the interference light beams detected by the n-channel interference light detecting device; and that the tomographic structure image generating device generates a tomographic structure image of the measuring object on the basis of each of the interference signals generated by the n-channel interference signal generating device.

An optical structure measuring apparatus according to a thirteenth aspect of the present invention is preferably such that in the optical structure measuring apparatus according to the twelfth aspect, when m is an integer of n or more, the irradiating device is configured by an m-surface light deflecting and irradiating device which has a substantially m-sided pyramid shape formed in such a manner that a vertex side of an m-sided pyramid having a planar m-sided polygon shaped bottom surface is cut at a predetermined height from the bottom surface, and which has m light deflecting surfaces that are formed by the side surfaces of the substantially m-sided pyramid, and that are arranged to be rotatable about the longitudinal axis.

An optical structure measuring apparatus according to a fourteenth aspect of the present invention is preferably such that in the optical structure measuring apparatus according to the thirteenth aspect, when n=2, m is set as m=3.

An optical probe of the optical structure measuring apparatus according to the fifteenth aspect is configured by including a thin and long sheath whose distal end is closed, an n-channel waveguide device in which n is an integer of three or more and which is inserted and fixed in the sheath along a longitudinal axis of the sheath so as to guide optical light beams, an irradiating device which is provided in a distal end portion of the sheath and which deflects a light beam emitted from each of the channels of the re-channel waveguide device in a radial direction about the longitudinal axis of the sheath to irradiate a measuring object with the deflected light beam, a rotating device which rotates the irradiating device about the longitudinal axis, and a forward/backward moving device which moves the n-channel waveguide device and the irradiating device forward and backward in the direction along the longitudinal axis.

An optical probe of an optical structure measuring apparatus according to a fifteenth aspect of the present invention, the radial scanning for acquiring optical structure information of the measuring object can be performed at high speed and the S/N ratio can be improved in such a manner that in the case where n is an integer of three or more, the n-channel waveguide device is inserted and fixed in the sheath along a longitudinal axis of the sheath so as to guide light beams, that the irradiating device deflects the light beam emitted from each of the channels of the n-channel waveguide device in a radial direction about the longitudinal axis of the sheath and irradiates the measuring object with the deflected light beam, that the rotating device rotates the irradiating device about the longitudinal axis, and that the forward/backward moving device moves the n-channel waveguide device and the irradiating device forward and backward in the direction along the longitudinal axis.

An optical probe of an optical structure measuring apparatus according to a sixteenth aspect of the present invention is preferably such that in the optical probe of the optical structure measuring apparatus according to the fifteenth aspect, the irradiating device is configured by an n-surface light deflecting and irradiating device which has a substantially n-sided pyramid shape formed in such a manner that a vertex side of an n-sided pyramid having a planar n-sided polygon shaped bottom surface is cut at a predetermined height from the bottom surface, and which has n light deflecting surfaces that are formed by the side surfaces of the substantially n-sided pyramid, and that are arranged to be rotatable about the longitudinal axis.

An optical probe of an optical structure measuring apparatus according to a seventeenth aspect of the present invention is preferably such that in the optical probe of the optical structure measuring apparatus according to the sixteenth aspect, the planar n-sided polygon shape is formed into a rotationally symmetrical shape about the longitudinal axis.

An optical probe of an optical structure measuring apparatus according to a eighteenth aspect of the present invention is preferably such that in the optical probe of the optical structure measuring apparatus according to one of the fifteenth to seventeenth aspects, the rotating device is configured by a torque transmitting coil, a distal end of which is integrally connected to the rotation center of the n-surface light deflecting and irradiating device, and which is rotatably inserted in the sheath along the longitudinal axis of the sheath, and a motor, a rotary shaft of which is connected to the proximal end of the torque transmitting coil, and which rotates the torque transmitting coil about the longitudinal axis.

An optical probe of an optical structure measuring apparatus according to an nineteenth aspect of the present invention is preferably such that in the optical probe of the optical structure measuring apparatus according to one of the fifteenth to seventeenth aspects, the rotating device is configured by a motor which is provided in the sheath on the distal end side from the n-surface light deflecting and irradiating device, and which uses, as its rotary shaft, the longitudinal axis integrally connected to the rotation center of the n-surface light deflecting and irradiating device.

An optical probe of an optical structure measuring apparatus according to a twentieth aspect of the present invention, the radial scanning for acquiring optical structure information of the measuring object can be performed at high speed and the S/N ratio can be improved in such a manner that in the case where n is an integer of two or more, the n-channel waveguide device is inserted and fixed in the sheath along a longitudinal axis of the sheath so as to guide light beams, that the irradiating device deflects the light beam emitted from each of the channels of the n-channel waveguide device in a radial direction about the longitudinal axis of the sheath and irradiates the measuring object with the deflected light beam, that the rotating device rotates the irradiating device about the longitudinal axis, and that the forward/backward moving device moves the n-channel waveguide device and the irradiating device forward and backward in the direction along the longitudinal axis.

An optical probe of an optical structure measuring apparatus according to a twenty first aspect of the present invention is preferably such that in the optical probe of the optical structure measuring apparatus according to the twentieth aspect, when m is an integer of n or more, the irradiating device is configured by an m-surface light deflecting and irradiating device which has a substantially m-sided pyramid shape formed in such a manner that the vertex side of an m-sided pyramid having a planar m-sided polygon shaped bottom surface is cut at a predetermined height from the bottom surface, and which has m light deflecting surfaces that are formed by the side surfaces of the substantially m-sided pyramid, and that are arranged to be rotatable about the longitudinal axis.

An optical probe of an optical structure measuring apparatus according to a twenty second aspect of the present invention is preferably such that in the optical probe of the optical structure measuring apparatus according to the twenty first aspect, when n=2, m is set as m=3.

According to the present invention, it is possible to obtain the effects that the radial scanning for acquiring optical structure information of a measuring object is performed at high speed, and that the S/N ratio is improved.

DETAILED DESCRIPTION OF THE PREFERRED EMBODIMENTS

In the following, an embodiment of an optical structure measuring apparatus according to the present invention will be described in detail with reference to the accompanying drawings.

<External Appearance of Image Diagnostic Apparatus>

Figure 1:
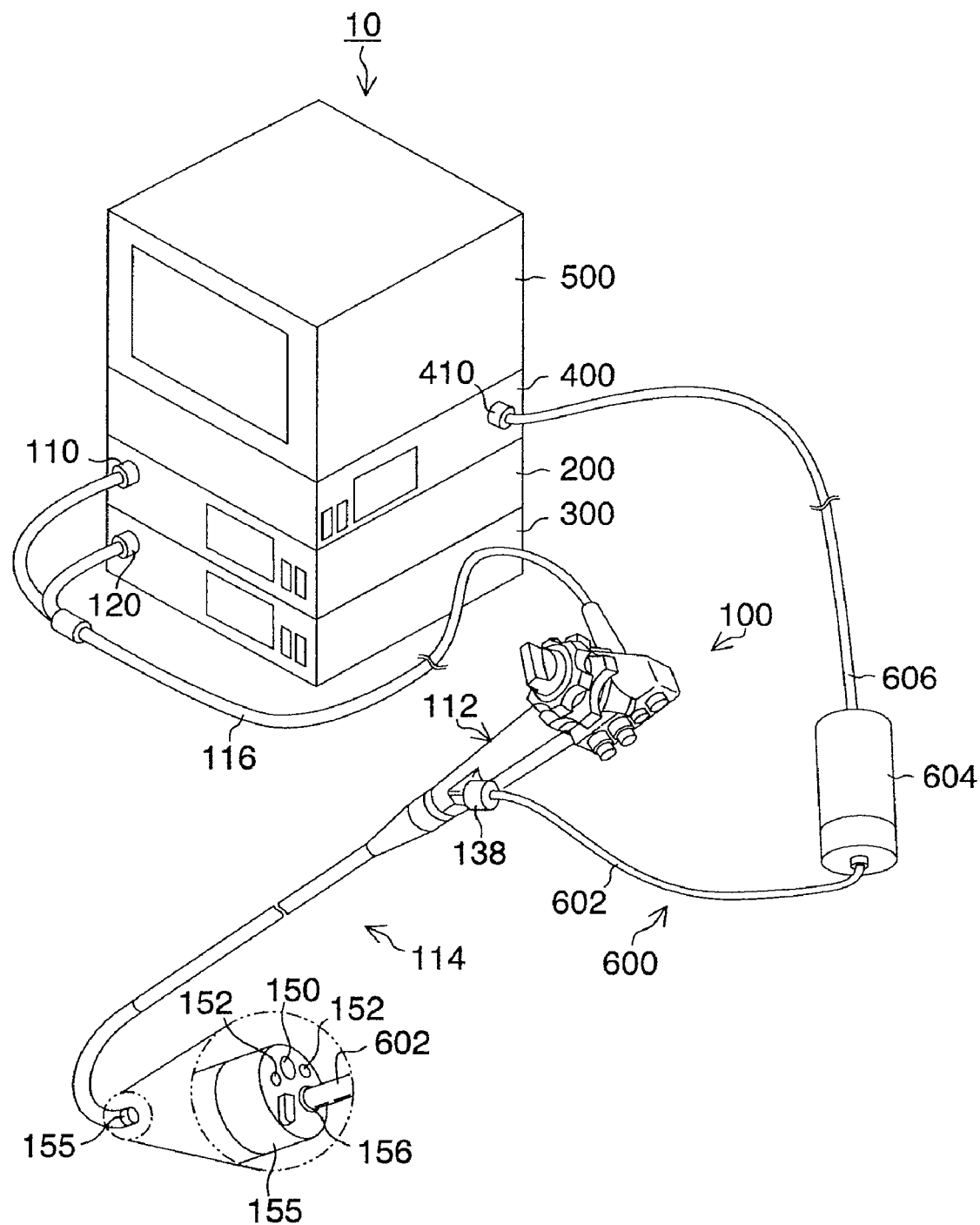
FIG. 1 is an external view showing an image diagnostic apparatus according to an embodiment of the present invention.

FIG. 1 is an external view showing an image diagnostic apparatus according to an embodiment of the present invention.

As shown in FIG. 1, an image diagnostic apparatus 10 according to the present embodiment is mainly configured by an endoscope 100, an endoscope processor 200, and a light source apparatus 300, an OCT processor 400 as an optical structure measuring apparatus, and an image display section 500 which is a monitoring apparatus. Note that the endoscope processor 200 may be configured so as to incorporate the light source apparatus 300 therein.

The endoscope 100 includes a hand operation part 112 and an insertion section 114 continuously connected to the hand operation part 112. An operator grasps and operates the hand operation part 112, and inserts the insertion section 114 into the body of a subject to thereby observe the inside of the body.

An forceps insertion section 138 is provided at the hand operation part 112. The forceps insertion section 138 is made to communicate with an forceps port 156 at a distal end section 155 via a forceps channel (not shown) provided in the insertion section 114. In the image diagnostic apparatus 10, an OCT probe 600 as an optical probe is inserted from the forceps insertion section 138 and thereby the OCT probe 600 is led out from the forceps channel 156. The OCT probe 600 is configured by an insertion section 602 which is inserted from the forceps insertion section 138 and led out from the forceps channel 156, an operation section 604 which is used by the operator to operate the OCT probe 600, and a cable 606 which is connected to the OCT processor 400 via a connector 410.

<Configuration of Endoscope, Endoscope Processor, and Light Source Apparatus>

[Endoscope]

An observation optical system 150, an illumination optical system 152, and a CCD (not shown) are arranged at the distal end section 155 of the endoscope 100.

The observation optical system 150 forms an image of the subject on the light receiving surface of the CCD (not shown) which converts the subject image formed on the light receiving surface thereof to electric signals by respective light receiving elements. The CCD of the present embodiment is a color CCD in which color filters of three primary colors of red (R), green (G), and blue (B) are arranged for each pixel in a predetermined array (Bayer array, honeycomb array).

[Light Source Apparatus]

The light source apparatus 300 makes visible light incident on a light guide (which is not shown and incorporated in a cable 116 of the endoscope 100). One end of the light guide is connected to the light source apparatus 300 via an LG connector 120, and the other end of the light guide is arranged to face the illumination optical system 152. A light beam emitted from the light source apparatus 300 is emitted from the illumination optical system 152 via the light guide, so as to illuminate the visual field range of the observation optical system 150.

[Endoscope Processor]

An image signal outputted from the CCD is inputted into the endoscope processor 200 via the cable 116 of the endoscope 10 and an electric connector 110. In the endoscope processor 200, the analog image signal is converted into a digital image signal which is then subjected to necessary processing so as to be displayed on the screen of the image display section 500.

In this way, the data of the observed image obtained by the endoscope 100 are outputted to the endoscope processor 200, so that an image is displayed in the image display section 500 connected to the endoscope processor 200.

<Configuration of OCT Probe and OCT Processor>

[OCT Probe]

Figure 2:
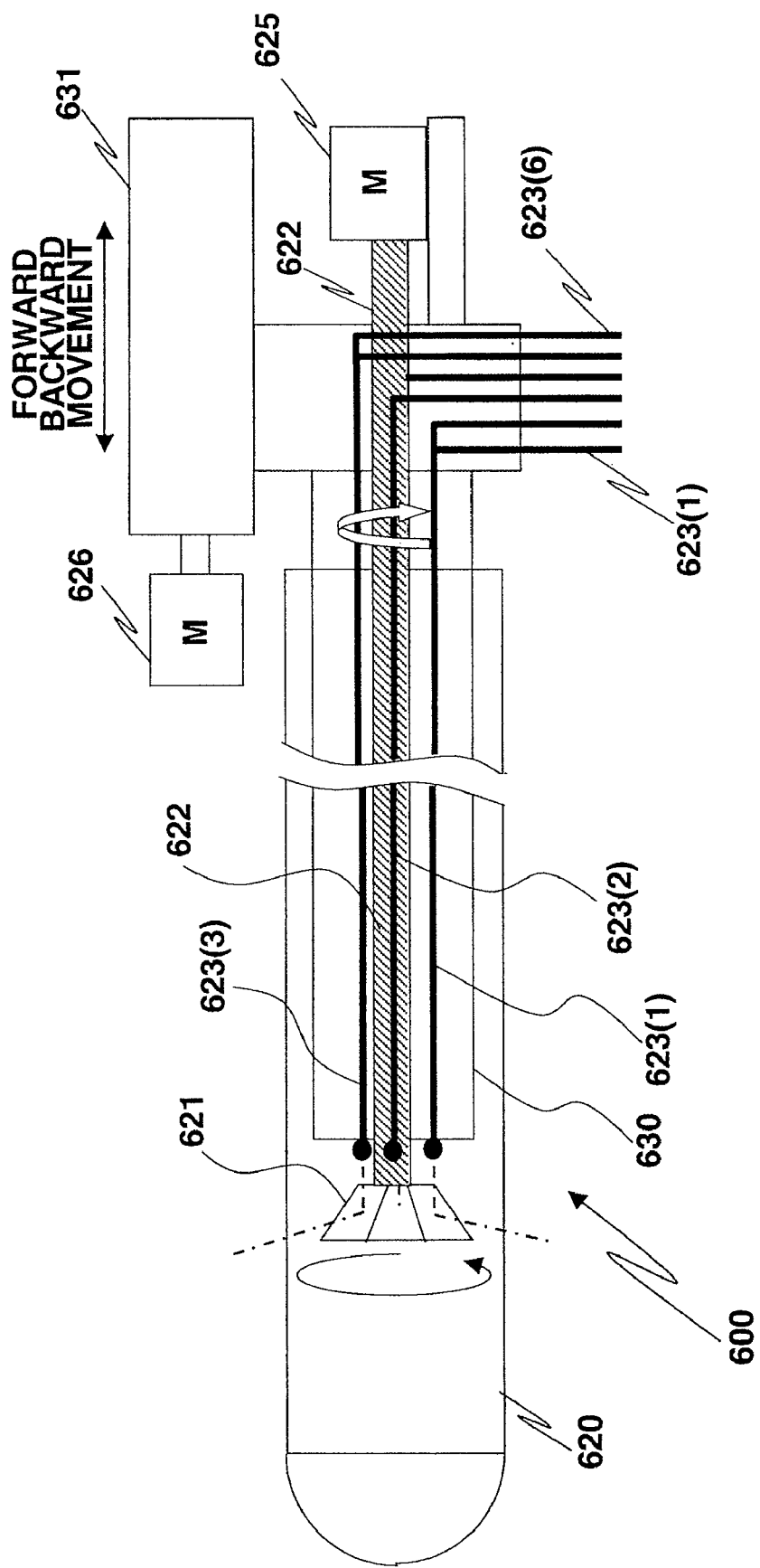
FIG. 2 is a view showing a configuration of an OCT probe connected to the OCT processor of FIG. 1.
Figure 3:
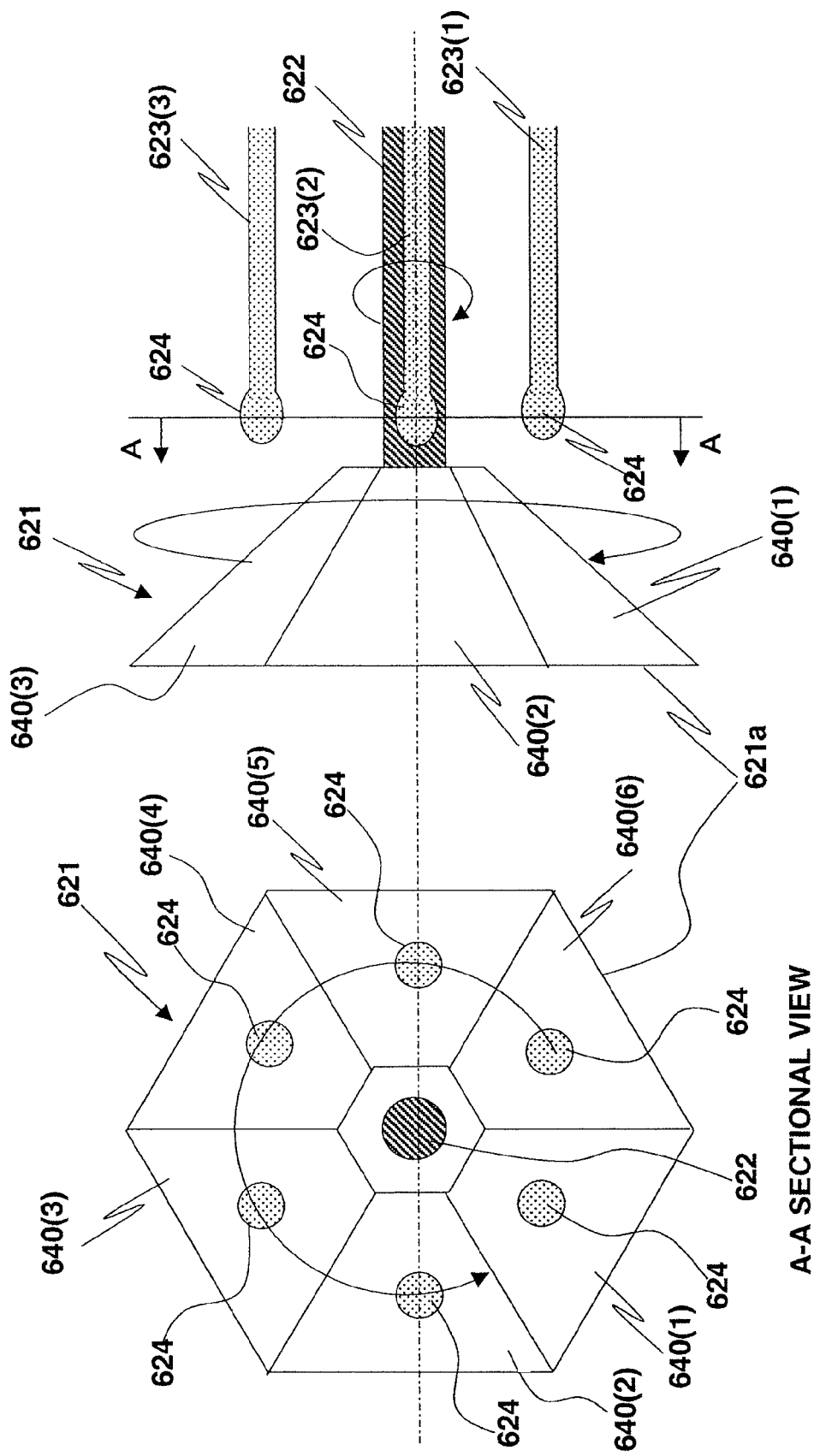
FIG. 3 is a view showing a detailed configuration of the n-reflecting surface body of FIG. 2.
Figure 4:
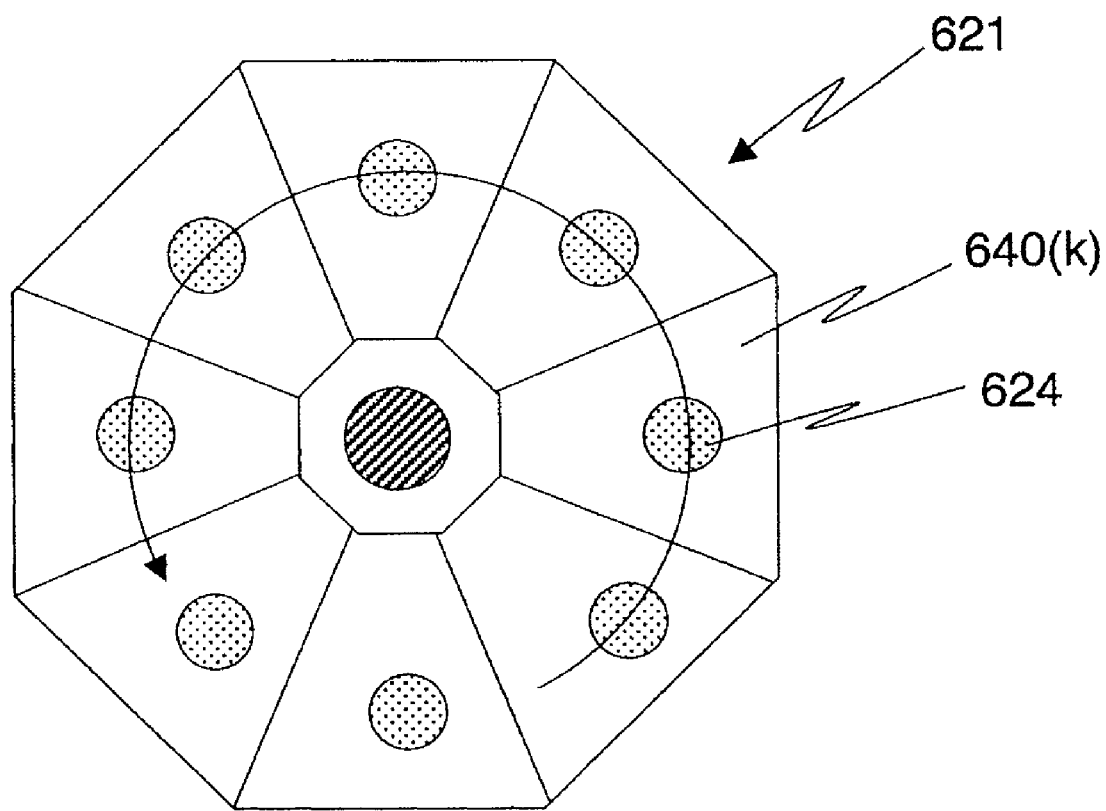
FIG. 4 is a view showing a configuration of a first modification of the n-reflecting surface body of FIG. 3.
Figure 5:
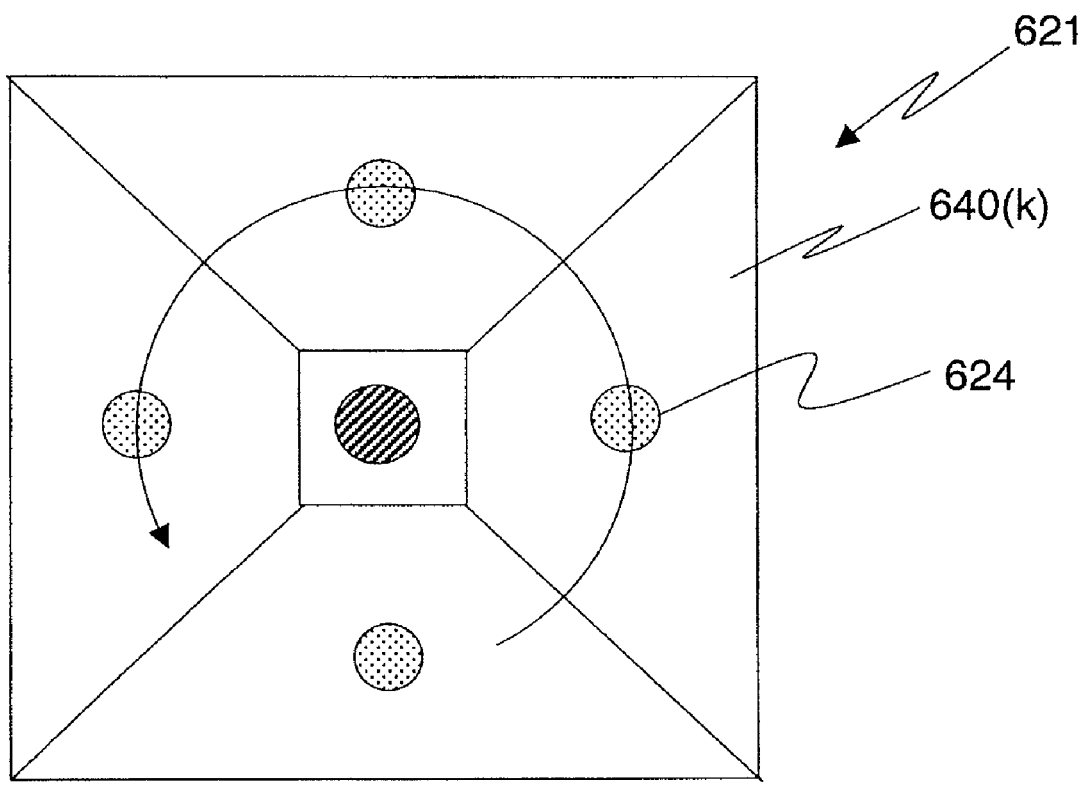
FIG. 5 is a view showing a configuration of a second modification of the n-reflecting surface body of FIG. 3.
Figure 6:
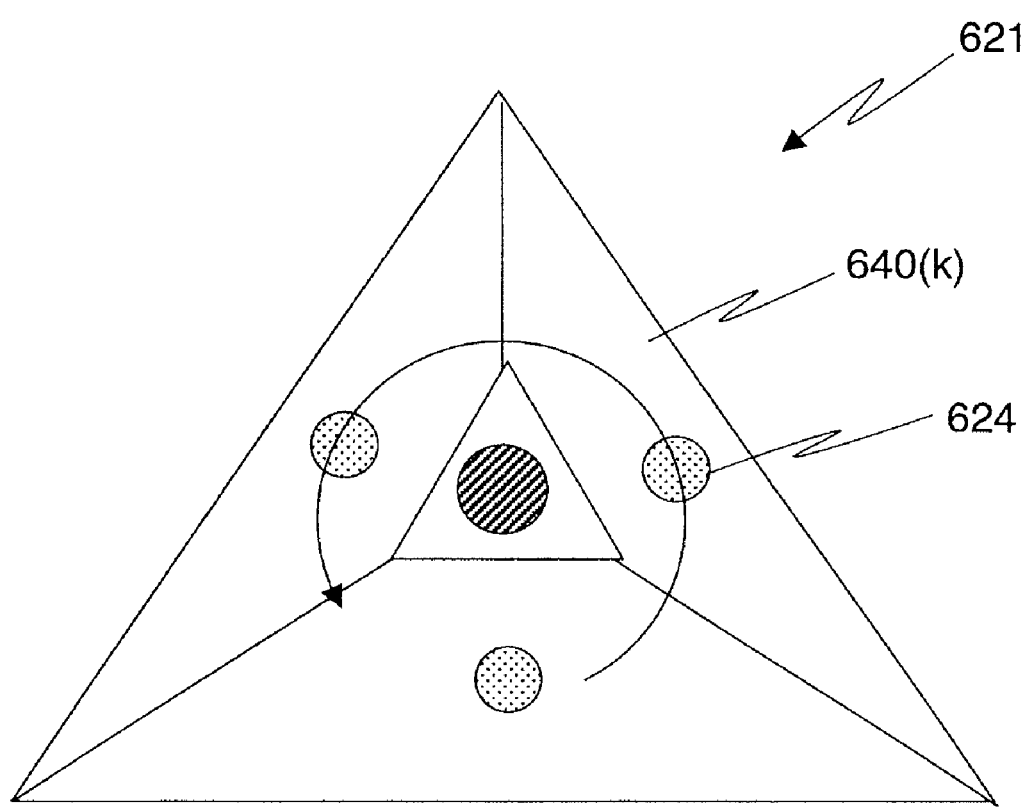
FIG. 6 is a view showing a configuration of a third modification of the n-reflecting surface body of FIG. 3.

FIG. 2 is a view showing a configuration of the OCT probe connected to the OCT processor shown in FIG. 1, and FIG. 3 is a view showing a detailed configuration of the n-reflecting surface body shown in FIG. 2. Further, FIG. 4 to FIG. 6 are views showing the configuration of modifications of the n-reflecting surface body shown in FIG. 3.

As shown in FIG. 2, the OCT probe 600 is configured by including: a thin and long substantially cylindrical sheath 620 whose distal end is closed; an n-reflecting surface body 621, as an irradiating device, which has n reflecting surfaces (with n being an integer of three or more) and which is provided at a distal end of the sheath 620; a torque transmitting coil 622, as a rotating device, which is provided along the longitudinal axis of the sheath 620 and which transmits rotational torque for rotating each of the reflecting surfaces of the n-reflecting surface body 621 about the longitudinal axis of the sheath 620; and n fibers 623(1) to 623($n$), as an n-channel waveguide device, which are provided and fixed in the sheath in a side by side relationship with the torque transmitting coil 622. In the following, for the sake of brevity of description, the present embodiment will be described on the assumption that n=6.

Each of the reflecting surfaces of the six-reflecting surface body 621 is arranged to face the distal end surface of each of the six channel fibers 623(1) to 623(6) at a predetermined angle (for example, 45 degrees, see FIG. 3), and a GRIN lens 624 as a light condensing device is provided at the distal end surface of each of the six channel fibers 623(1) to 623(6). Further, each of the light beams respectively guided through the six channel fibers 623(1) to 623(6) is condensed by the GRIN lens 624, and is reflected by each of the reflecting surfaces of the six-reflecting surface body 621 so as to be deflected in a radial direction about the longitudinal axis of the sheath 620.

The torque transmitting coil 622 is configured such that the distal end of the torque transmitting coil 622 is connected to the vertex side of the six-reflecting surface body 621, and such that the proximal end of the torque transmitting coil 622 is integrally connected to a motor 625 using, as its rotary shaft, the longitudinal axis of the sheath 620.

The six channel fibers 623(1) to 623(6), the six-reflecting surface body 621, and the torque transmitting coil 622 configure a sheath-enclosed member 630 which is enclosed and inserted in the OCT probe 600. The sheath-enclosed member 630 is connected to a forward/backward driving mechanism section 631, as a forward/backward moving device, which is driven forward and backward in the longitudinal axis direction of the sheath 620. The forward/backward driving mechanism section 631 is configured by a ball screw (not shown), and the like, and is configured such that the rotational driving force of a motor 626 is converted into the forward and backward driving force to thereby drive the sheath enclosed member 630 forward and backward in the longitudinal axis direction of the sheath 620.

Here, the six channel fibers 623(1) to 623(6) are fixed so as not to be rotated in the sheath 620, and hence an optical rotary joint is not needed. Thus, by rotating the respective reflecting surfaces of the six-reflecting surface body 621 by the torque transmitting coil 622, it is possible to perform the radial scanning of the light beams from the six channel fibers 623(1) to 623(6).

As shown in FIG. 3, the six-reflecting surface body 621 is configured to have a substantially six-sided pyramid shape formed in such a manner that the vertex side of a regular six-sided pyramid having a planar regular six-sided polygon shaped bottom surface 621a is cut at a predetermined height from the bottom surface, and which has six light deflecting surfaces 640(1) to 640(6) that are formed by the side surfaces of the substantially six-sided pyramid, and that are arranged to be rotatable about the longitudinal axis of the sheath 620. The six-reflecting surface body 621 is formed into a rotationally symmetrical shape about the longitudinal axis of the sheath 620.

Therefore, each of the light beams from the six channel fibers 623(1) to 623(6) is condensed by the GRIN lens 624, and is reflected by each of the six light deflecting surfaces 640(1) to 640(6) so as to be irradiated in the radial direction.

At this time, by rotating the six-reflecting surface body 621 by 60 degrees (=360 degrees×⅙), it is possible to perform the radial scanning over the entire circumference of the sheath by the six light beams from the six channel fibers 623(1) to 623(6).

That is, when n is an integer of three or more and when the n-reflecting surface body 621 is rotated by "360 degrees×1/n", the radial scanning over the entire circumference of 360 degrees can be performed at high speed by the n light beams from the n channel fibers 623(1) to 623(n).

Note that an example where n=6 is described, but the present embodiment is not limited to this. For example, the bottom surface of the n-reflecting surface body may be formed into a planar regular octagon, as shown in FIG. 4, and may also be formed into a planar regular quadrangle as shown in FIG. 5 and a planar regular triangle as shown in FIG. 6. That is, it may be configured such that the n channel fibers 623(1) to 623(n) are arranged in correspondence with the n light deflecting surfaces 640(1) to 640(n) of the n-reflecting surface body.

[OCT Processor]

Figure 7:
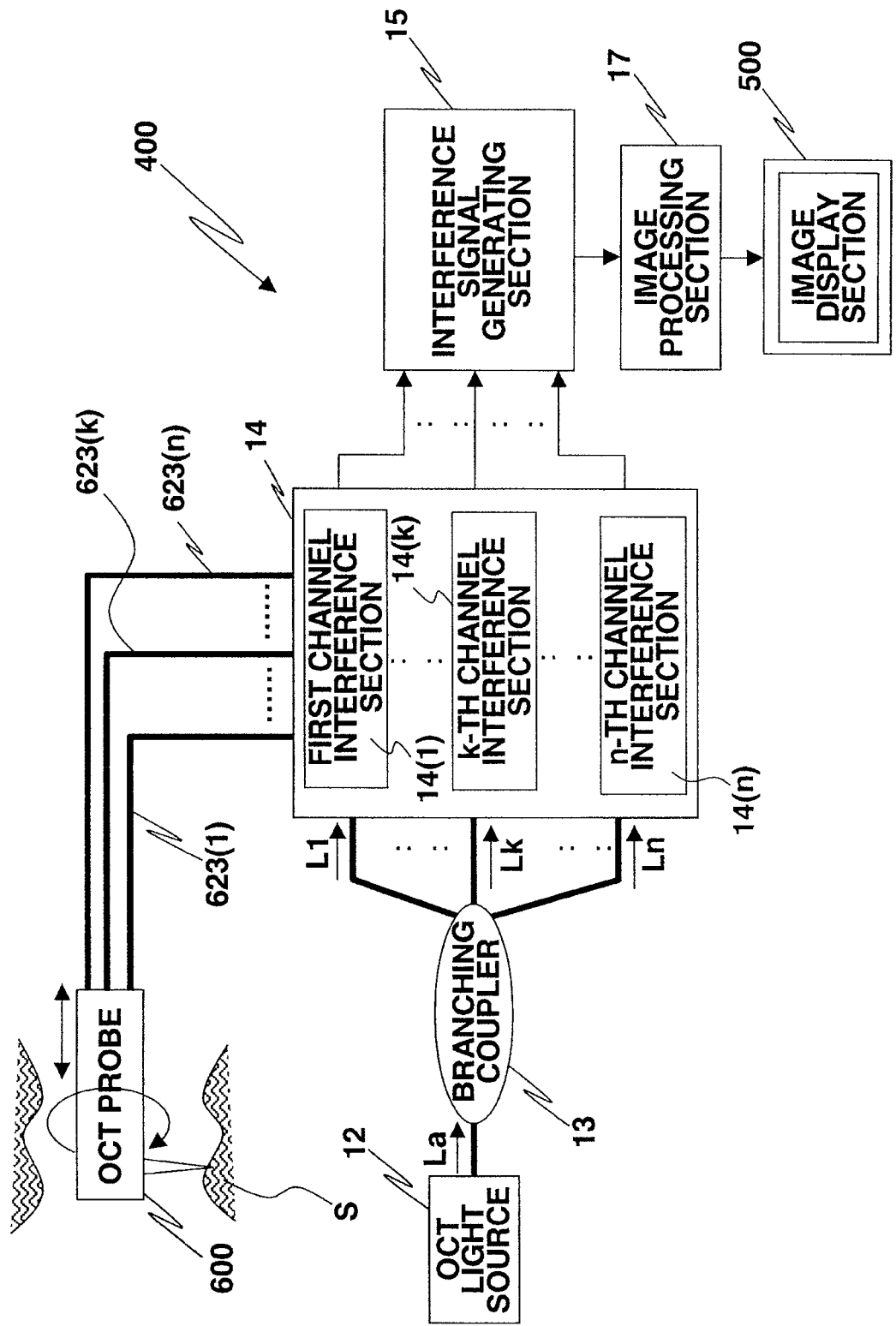
FIG. 7 is a block diagram showing a configuration of the OCT processor of FIG. 1.

FIG. 7 is a block diagram showing a configuration of the OCT processor shown in FIG. 1. As shown in FIG. 7, the OCT processor 400 is configured to acquire an optical tomographic image of a measuring object S on the basis of the optical coherence tomography (OCT) measuring method, and is configured by including: an OCT light source 12, as a light source device, which emits a light beam La for measurement; a branching coupler 13 which branches the light beam La emitted from the OCT light source 12 into n channel light beams L1 to Ln; an interference section 14, as an n-channel interference light detecting device, which is configured by a first to n-th channel interference sections 14(1) to 14(n) each of which branches each of the n channel light beams L1 to Ln into a measuring light beam and a reference light beam, to detect an interference wave; an interference signal generating section 15, as an n-channel interference signal generating device, which generates interference signals on the basis of the interference waves from the first to n-th channel interference sections 14(1) to 14(n) of the interference section 14; and an image processing section 17, as a tomographic structure image generating device and a three-dimensional structure image generating device, which generates tomographic structure images and a three-dimensional structure image of the measuring object S on the basis of the interference signals generated by the interference signal generating section 15, and which makes the tomographic structure images and the three-dimensional structure image displayed in the image display section 500.

Figure 8:
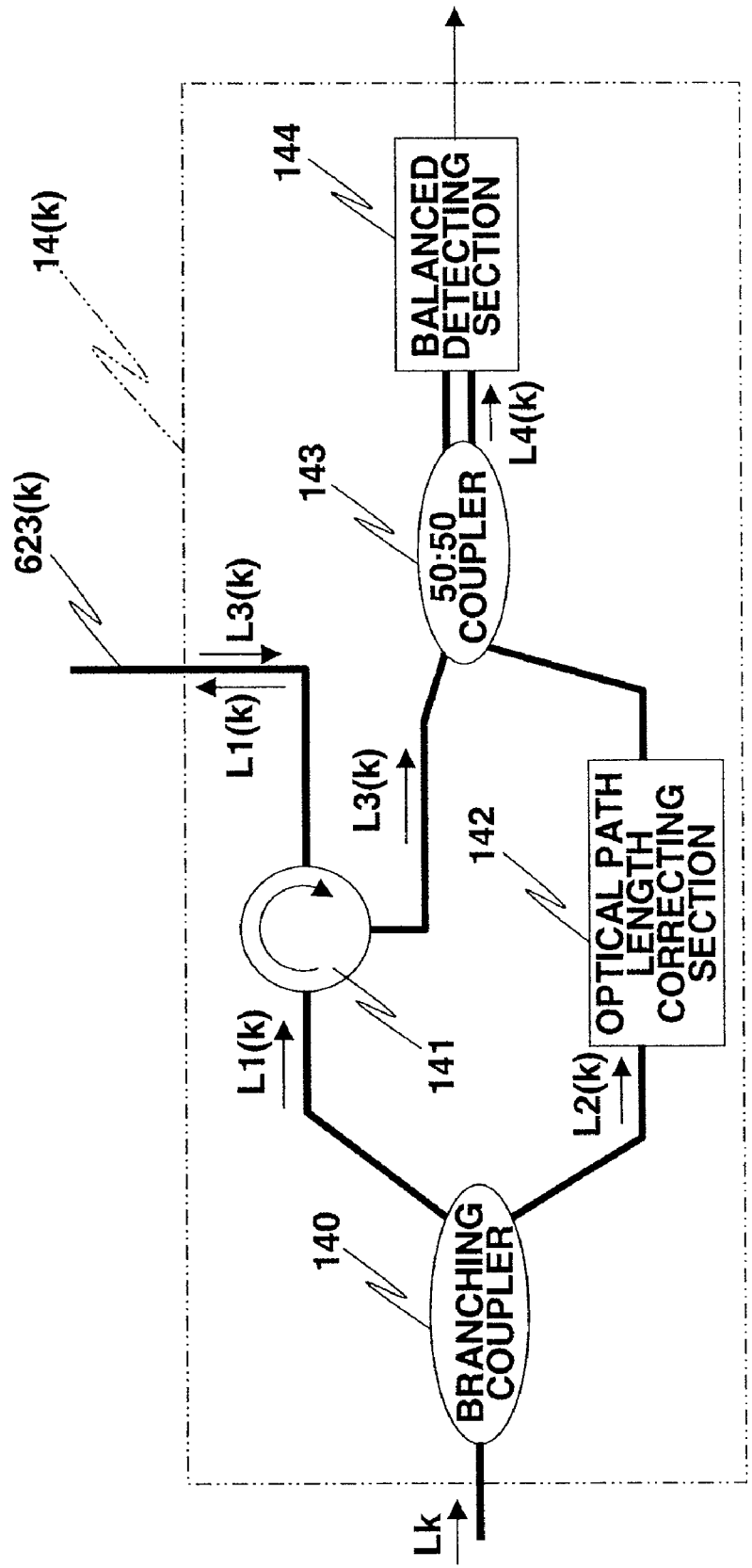
FIG. 8 is a block diagram showing a configuration of a k-th channel interference section in the interference section of FIG. 7.

In the following, for the sake of brevity of description, the present embodiment will be described by making the integers of 1 to n represented by k. FIG. 8 is a block diagram showing a configuration of the n-th channel interference section in the interference section shown in FIG. 7.

As shown in FIG. 8, the k-th channel interference section 14(k) in the interference section 14 is configured by including: a branching coupler 140, as a branching device and an n-channel branching device, which branches the light beam Lk branched by the branching coupler 13 to a measuring light beam L1(k) and a reference light beam L2(k); a circulator 141, as a branching and light guiding device, which guides the measuring light beam L1(k) to the k-channel fiber 623(k) of the OCT probe 600; an optical path length correcting section 142, as an optical path length correcting device, which corrects the length of the optical path for transmitting the reference light beam L2(k); a 50:50 coupler 143 in which a return light beam L3(k) transmitted from the measuring object S by the k-channel fiber 623(k) of the OCT probe 600 via the circulator 141 is made to interfere with the reference light beam L2(k) transmitted via the optical path length correcting section 142(k); and a balanced detecting section 144 which performs balanced detection of the interference light beam L4(k) formed by the interference of the beams in the 50:50 coupler 143, so as to output the detected signal to the interference signal generating section 15.

Figure 9:
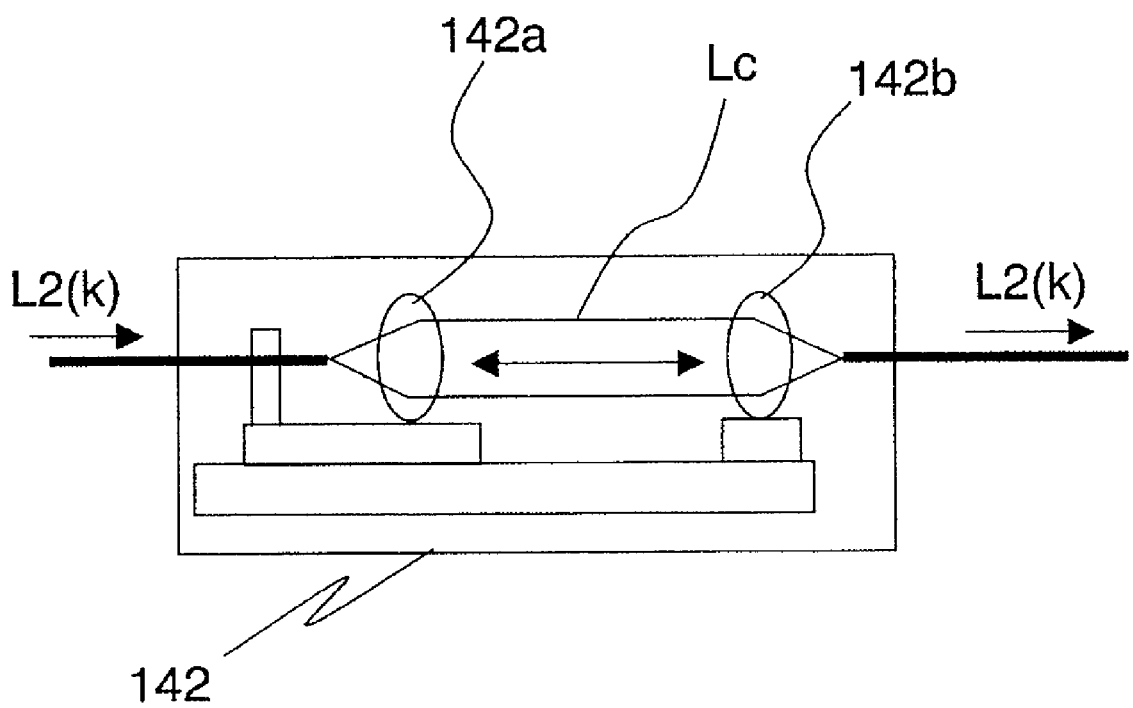
FIG. 9 is a view showing a configuration example of the optical path length correcting section of FIG. 8.

FIG. 9 is a view showing a configuration example of the optical path length correcting section shown in FIG. 8. The optical path length correcting section 142 for the reference light beam L2(k) is one of n optical path length (fine) adjusting devices which are respectively provided in the first to n-th channel interference sections 14(1) to 14(n) in order to adjust the zero-crossing position in the respective channels of the first to n-th channel interference sections 14(1) to 14(n). As shown in FIG. 9, the optical path length correcting section 142 is configured such that two collimator lenses 142a and 142b are used to change the space length for the collimated light beam Lc between the collimator lens 142a and 142b. Here, when the optical path length of one of the first to n-th channel interference sections 14(1) to 14(n) is set as a reference optical path length, the number of the optical path length correcting sections 142 can be reduced to n−1. Note that the optical path length correcting section may also be configured to change the optical path length by utilizing the birefringence.

The effects of the present embodiment configured in this way will be described.

The interference signal generating section 15 generates interference signals on the basis of the interference light beams L4(1) to L4(n) each of which is detected by the balanced detecting section 144 of each of the first to n-th channel interference sections 14(1) to 14(n). When the n-reflecting surface body 621 is rotated by 360/n degrees, the interference signal generating section 15 A/D-converts the interference signals by using, as a trigger, a wavelength sweep synchronizing signal outputted from the OCT light source 12 in synchronization with the wavelength sweep period. As a result, the data outputted from each of the first to n-th channel interference sections 14(1) to 14(n) in correspondence with one wavelength sweep can be obtained as a digitized interference signal for each 1/n-radial-scanning line.

Further, by applying fast Fourier transform (FFT) processing to the digitized interference signal obtained from each of the first to n-th channel interference sections 14(1) to 14(n) in correspondence with each 1/n-radial-scanning line, the interference signal generating section 15 frequency-decomposes the digitized interference signal, so as to obtain reflection intensity data in the depth direction of the measuring object S. Then, the interference signal generating section 15 performs logarithmic transformation of the reflection intensity data, to generate one-radial-scanning line data by combining the 1/n-radial-scanning line reflection intensity data respectively corresponding to the first to n-th channel interference sections 14(1) to 14(n), and outputs the generated one-radial-scanning line data to the image processing section 17.

Then, the image processing section 17 generates one frame of tomographic image by subjecting the reflection intensity data, which are the one-radial-scanning line data from the interference signal generating section 15, to brightness adjustment processing, contrast adjustment processing, gamma correction processing, re-sampling processing corresponding to a display size, coordinate conversion processing corresponding to the scanning method, and the like, so as to enable a tomographic image to be displayed in the image display section 500.

As described above, in the present embodiment, the OCT probe 600 is configured by a device which obtains a two-dimensional tomogram in the radial direction in such a manner that the n-reflecting surface body 621 connected to the torque transmitting coil 622 is rotated by the motor 625, and is configured by a device which obtains a three-dimensional tomogram in such a manner that the n-reflecting surface body 621, the motor 625, and the k-channel fiber 623(k) provided with the GRIN lens 624 are linearly scanned by the motor 626 in the longitudinal axis direction of the sheath 620. According to this configuration, the torque transmitting coil 622 is used as the rotary drive device, and hence the diameter of the distal end section of the probe can be reduced (for example, diameter<φ2.8 mm). Thus, a tomogram of the inside of a living body can be obtained by inserting the OCT probe 600 into the forceps insertion section 138 of the endoscope 100. In the case where the n channel interference signals are acquired by using the n-reflecting surface body, the radial direction signals for one round of the circumference can be acquired in a time period of 1/n times the time period when one reflecting body is usually used and rotated at the same rotation speed. Thereby, the signal acquisition speed can be improved.

In this way, the present embodiment has the following effects.

(1) The signal acquisition speed can be increased by n times by simultaneously performing one radial scanning for each of the n channels, so that tomographic structure images and a three-dimensional structure image can be acquired in a short time.

(2) The optical fibers are fixed in the OCT probe so as to be separated from the rotary mirror. Thereby, the conventionally required optical rotary joint can be made unnecessary, with the result that the reflection loss of the measuring light beam and the return light beam in the optical rotary joint can be eliminated and thereby the S/N ratio can be improved.

Note that in the present embodiment, it is assumed that the sheath enclosed member 630 is moved forward and backward in the longitudinal axis direction of the sheath 620, but the present embodiment is not limited to this. It may also be configured such that the OCT probe 600 as a whole is moved forward and backward in the longitudinal axis direction of the sheath 620.

The present embodiment can be configured as shown by following modifications 1 and 2.

Figure 10:
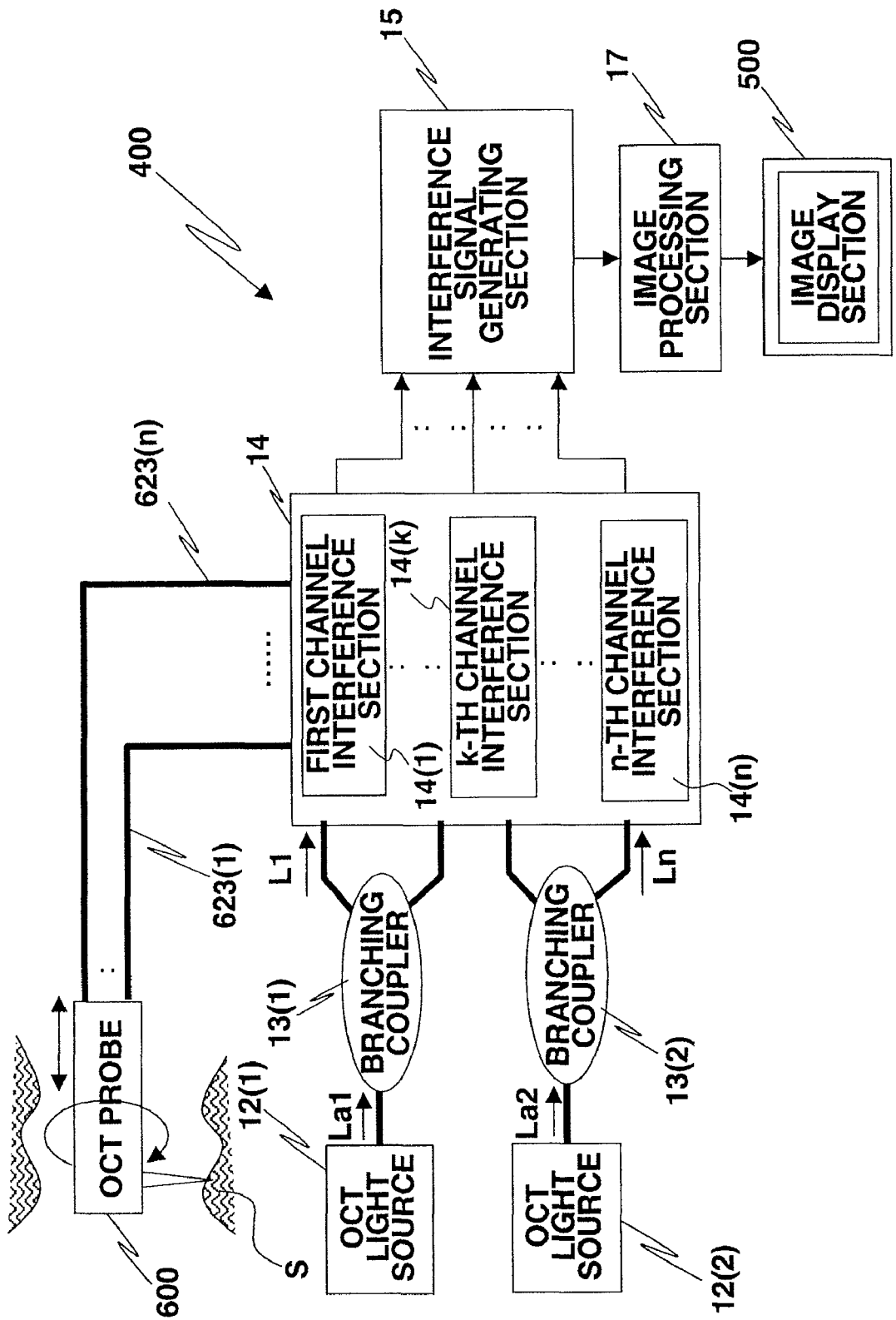
FIG. 10 is a block diagram showing a configuration of modification 1 of the OCT processor of FIG. 7.

(A) Modification 1: FIG. 10 is a block diagram showing a configuration of modification 1 of the OCT processor shown in FIG. 7.

In the present embodiment, the light beam La from the one OCT light source 12 is branched into the light beams L1 to Ln for the n channels by the branching coupler 13. However, as shown in FIG. 10, in order to secure light quantity necessary for the observation of a living body, the modification 1 of the present embodiment may be configured such that a plurality of, for example, two sets of an OCT light source and a branching coupler, that is, a set of an OCT light source 12(1) and a branching coupler 13(1), and a set of an OCT light source 12(2) and a branching coupler 13(2), are used, and such that light beams La1 and La2 from the OCT light sources 12(1) and 12(2) are branched into the light beams L1 to Ln for the n channels by the branching couplers 13(1) and 13(2). Further, although not shown, in order to secure the light quantity, it may also be configured such that n sets of the OCT light source and the branching coupler are respectively arranged for the first to n-th channel interference sections 14(1) to 14(n).

It goes without saying that the operating effects similar to those in the present embodiment can be obtained even in modification 1.

Figure 11:
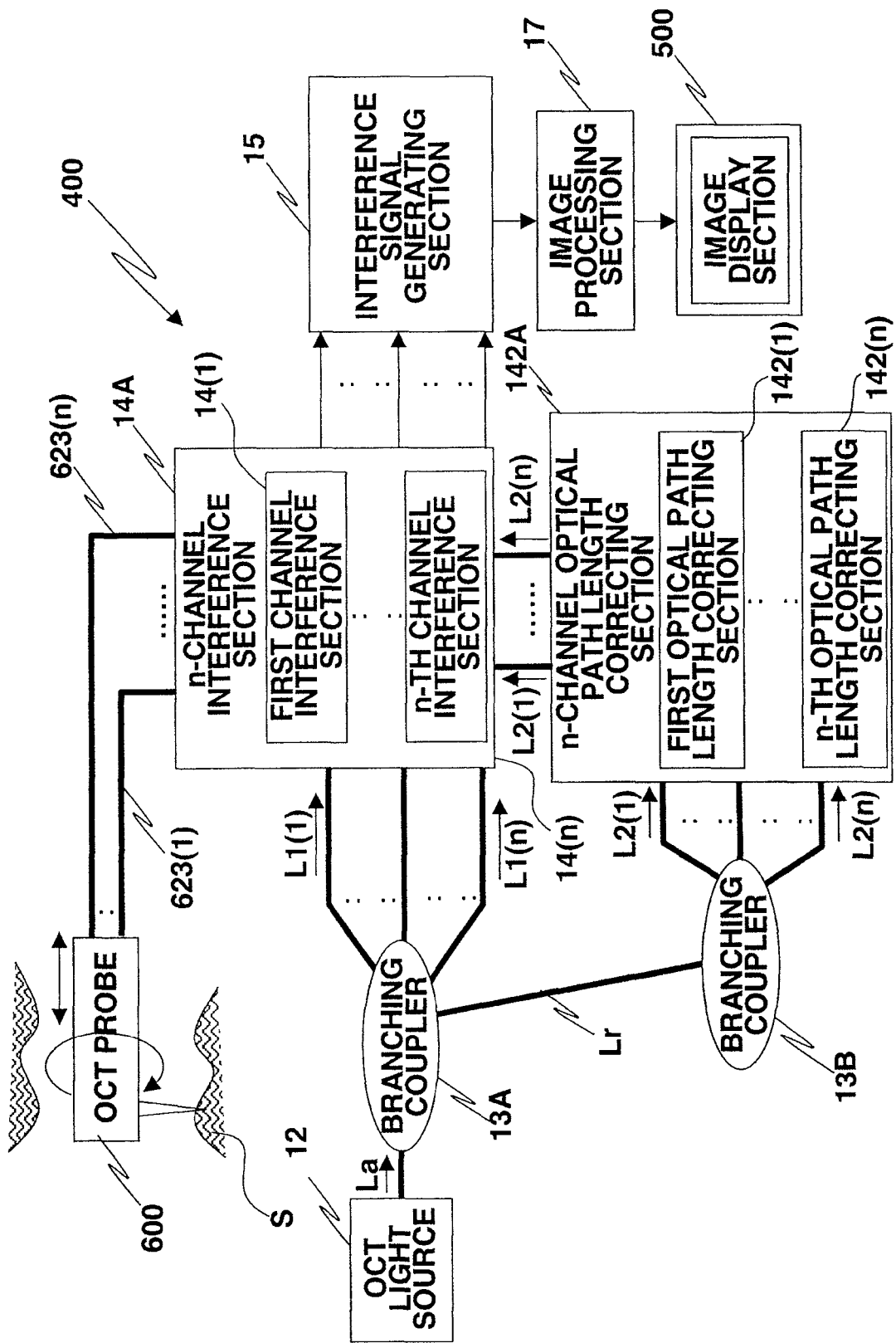
FIG. 11 is a block diagram showing a configuration of modification 2 of the OCT processor of FIG. 7.

(B) Modification 2: FIG. 11 is a block diagram showing a configuration of modification 2 of the OCT processor shown in FIG. 7, and FIG. 12 is a block diagram showing a configuration of the k-th channel interference section and the k-th optical path length correcting section shown in FIG. 11.

As shown in FIG. 11, the OCT processor 400 of modification 2 is configured by including a branching coupler 13A which branches a light beam La from the OCT light source 12 into n channel measuring light beams L1(1) to L1(n) and one reference light beam Lr, and a branching coupler 13B, as an n-channel reference light branching device, which further branches the reference light beam Lr into n channel reference light beams L2(1) to L2(n). Further, the OCT processor 400 of modification 2 is configured by including: an n-channel interference section 14A that is configured by the first to n-th channel interference sections 14(1) to 14(n) from each of which the optical path length correcting section 142 is removed; and an n-channel optical path length correcting section 142A that is configured by first to n-th optical path length correcting sections 142(1) to 142(n) in such a way that the optical path length correcting sections corresponding to the first to n-th channel interference sections 14(1) to 14(n) are separated from the first to n-th channel interference sections 14(1) to 14(n).

Figure 12:
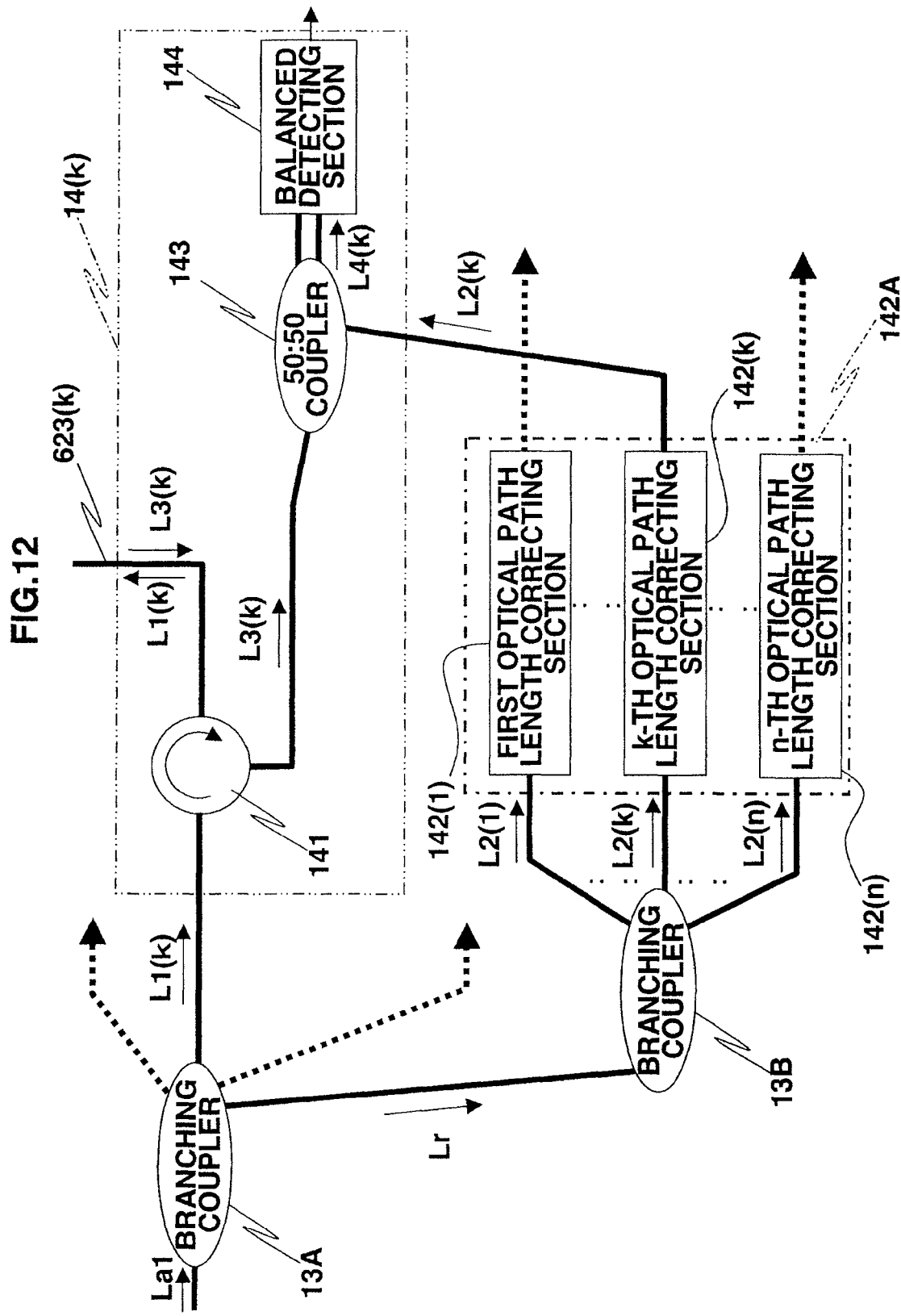
FIG. 12 is a block diagram showing a configuration of the k-th channel interference section and the k-th optical path length correcting section of FIG. 11.

As shown in FIG. 12, the k-th channel interference section 14(k) of the n-channel interference section 14A is configured by the circulator 141, the 50:50 coupler 143, and the balanced detecting section 144. Further, the n-channel optical path length correcting section 142A is configured by the n optical path length correcting sections 142 each of which corrects the length of optical path for transmitting the reference light beam L2(k).

With this configuration, similarly to the above described present embodiment, the OCT processor 400 in modification 2 operates in such a manner that the measuring light beam L1(k) from the branching coupler 13A is guided to the k-channel fiber 623(k) of the OCT probe 600 by the circulator 141, that the length of optical path for transmitting the reference light beam L2(k) from the branching coupler 13B is corrected in the k-th optical path length correcting section 142(k) of the n-channel optical path length correcting section 142A, that in the 50:50 coupler 143, the return light beam L3(k) transmitted from the measuring object S through the k-channel fiber 623(k) of the OCT probe 600 and through the circulator 141 is made to interfere with the reference light beam L2(k) transmitted through the k-th optical path length correcting section 142(k) of the n-channel optical path length correcting section 142A, and that in the balanced detecting section 144, the interference light beam L4(k) formed by the interference of the light beams in the 50:50 coupler 143 is subjected to balanced detection so as to be outputted to the interference signal generating section 15.

It goes without saying that the effects similar to those in the present embodiment can be obtained even in modification 2.

Note that when the optical path length of one of the first to n-th channel interference sections 14(1) to 14(n) is set as a reference optical path length, the number of the optical path length correcting sections 142 can be reduced to n−1. Note that the optical path length correcting section may also be configured to change the optical path length by utilizing the birefringence.

Figure 13:
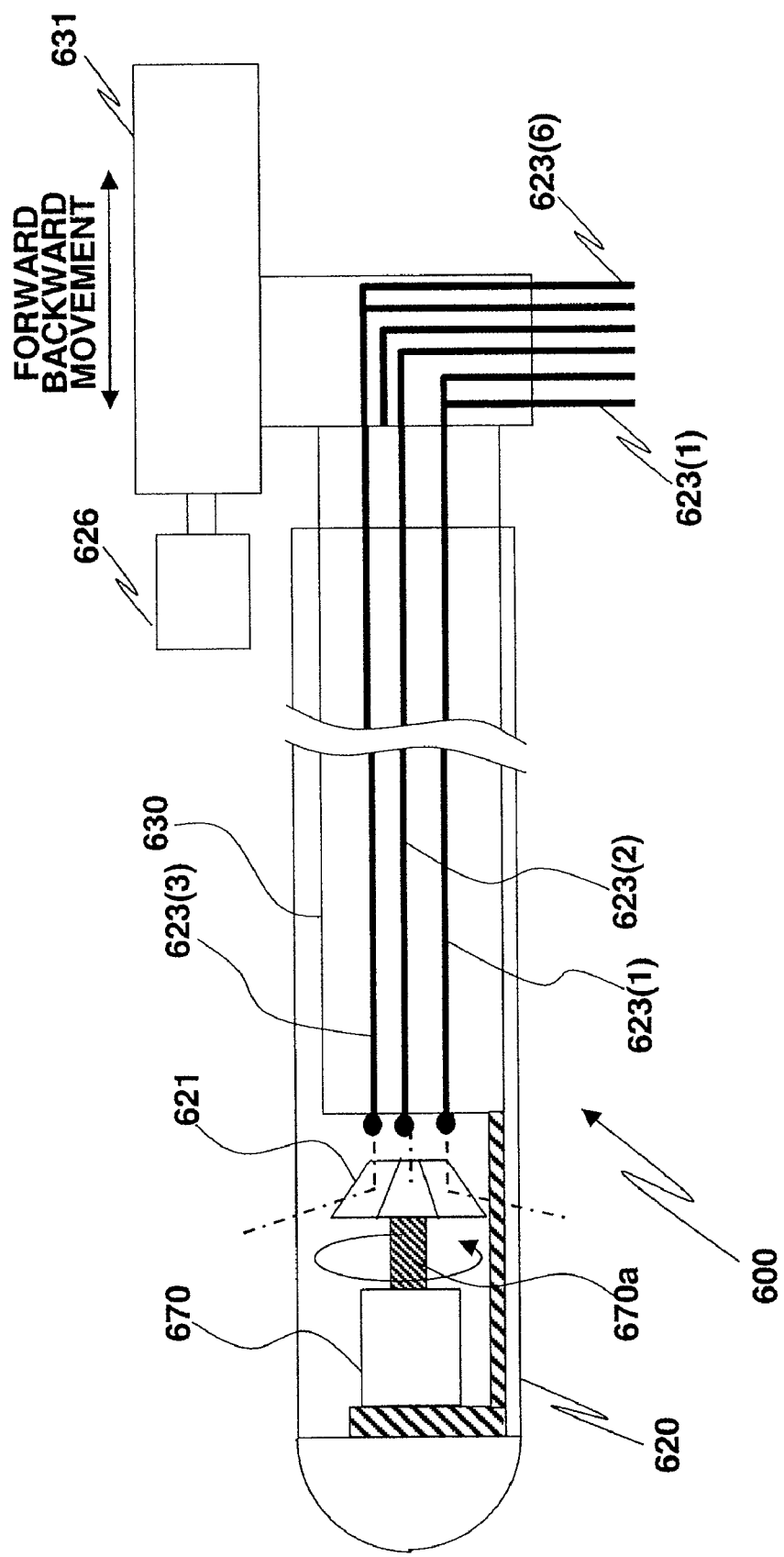
FIG. 13 is a view showing a configuration of a modification of the OCT probe of FIG. 2.

In the present embodiment, the OCT probe 600 is configured by including: the thin and long substantially cylindrical sheath 620 whose distal end is closed; the n-reflecting surface body 621 which has n reflecting surfaces (with n being an integer of three or more) provided at the distal end of the sheath 620; the torque transmitting coil 622 which is provided along the longitudinal axis of the sheath 620 and which transmits rotational torque for rotating each of the reflecting surfaces of the n-reflecting surface body 621 about the longitudinal axis of the sheath 620; and the n fibers 623(1) to 623(n) which are provided and fixed in the sheath in the side by side relationship with the torque transmitting coil 622 (see FIG. 2). However, the present embodiment is not limited to this and may also be configured as shown in FIG. 13. FIG. 13 is a view showing a configuration of a modification of the OCT probe shown in FIG. 2.

That is, as shown in FIG. 13, the OCT probe 600 may be configured such that a micro motor 670 integrally connected to the sheath-enclosed member 630 is provided in the distal end of the sheath 620 so that the radial direction scanning about the longitudinal axis of the sheath 620 is performed by rotating the n-reflecting surface body 621 by the motor shaft 670a of the micro motor 670.

Figure 14:
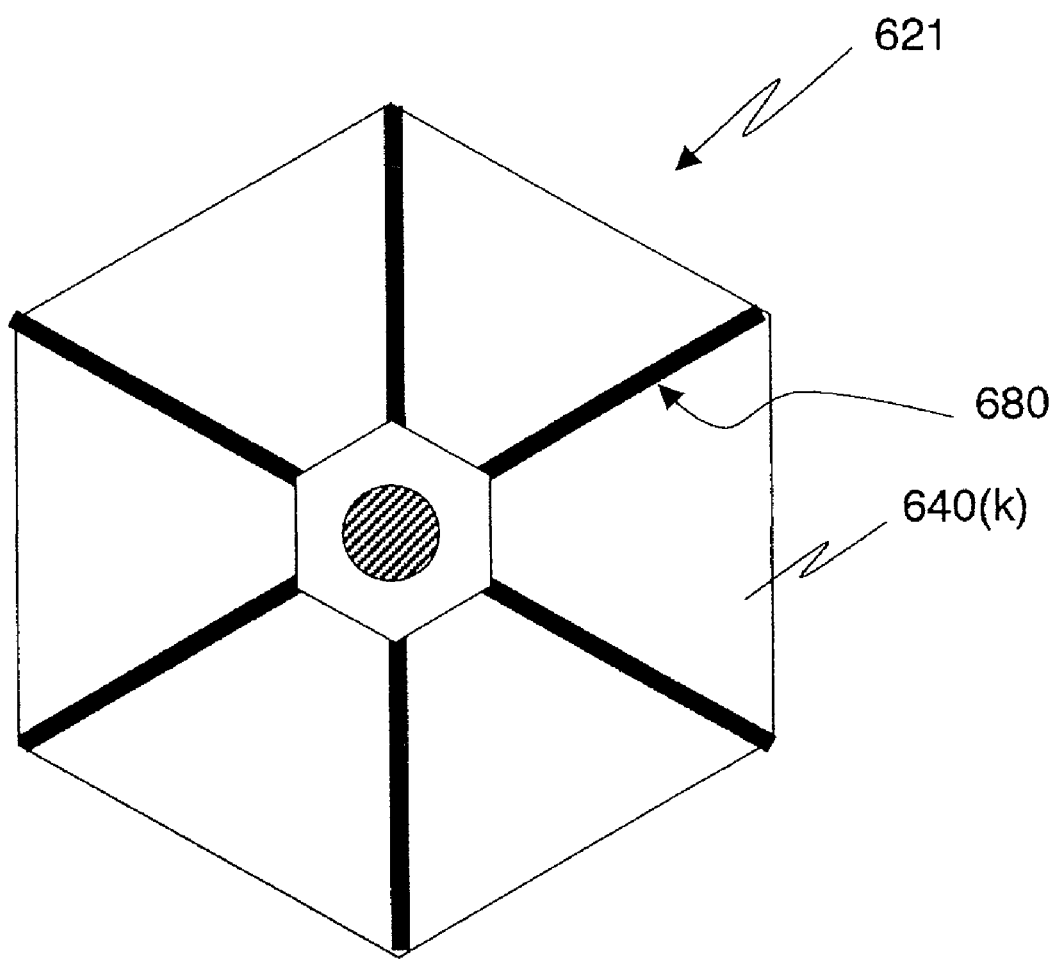
FIG. 14 is a view showing a mask member which can be arranged at the boundary between the reflection surfaces of the n-reflecting surface body of FIG. 3.

FIG. 14 is a view showing a mask member which can be arranged at the boundary between the reflecting surfaces of the n-reflecting surface body shown in FIG. 3. As shown in FIG. 14, at the boundary section of the light deflecting surface 640(k) of the n-reflecting surface body 621, a noise is generated because the light beam is not collected and a tomogram is not obtained. Thus, it may also be configured such that the influence of the noise is suppressed by adding a low reflection mask 680 to the boundary section.

Figure 15:
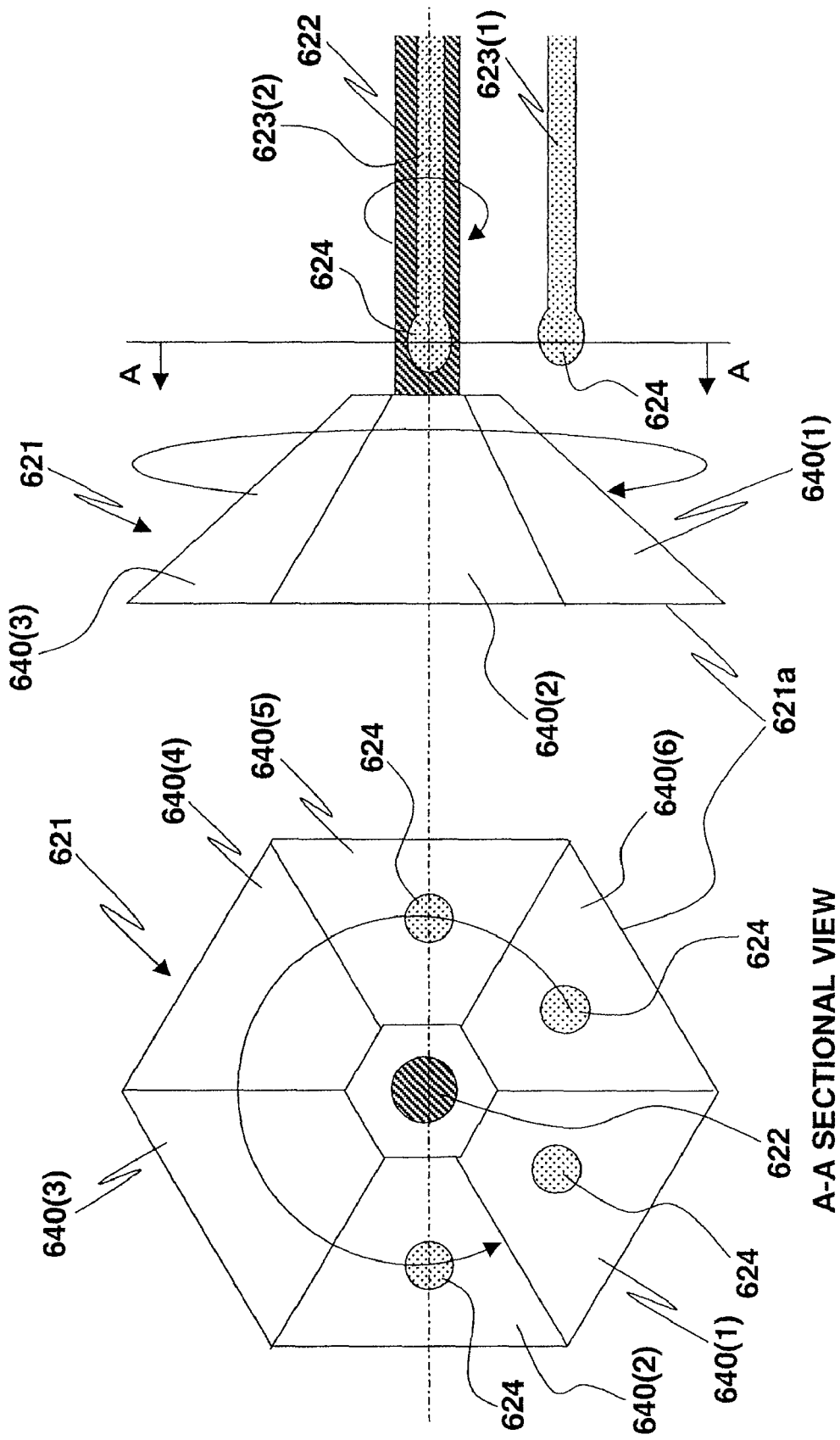
FIG. 15 is a view showing a modification of the channel fiber arrangement in the OCT probe of FIG. 2.
Figure 16:
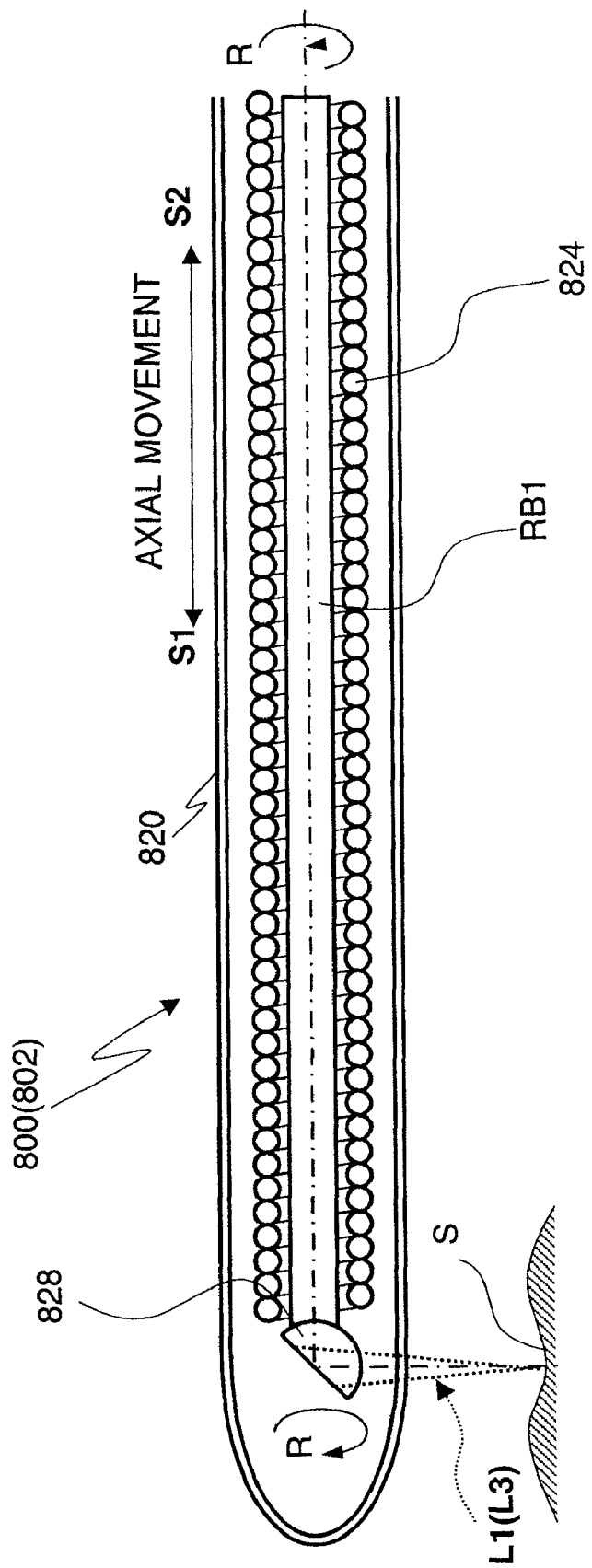
FIG. 16 is a view showing an OCT probe used for the conventional OCT measurement.

FIG. 15 is a view showing a modification of the arrangement of the channel fibers in the OCT probe shown in FIG. 2. The present embodiment is configured such that each of the reflecting surfaces of the n-reflecting surface body 621 is arranged to face the distal end of each of the n fibers 623(1) to 623(n) at a predetermined angle (for example, 45 degrees), but the present embodiment is not limited to this. As shown in FIG. 15, it may also be configured such that, for example, the distal ends of the four fibers 623(1) to 623(4) are arranged to face the reflecting surfaces of the six-reflecting surface body 621 at a predetermined angle (for example, 45 degrees). In this case, the radial scanning cannot be performed over the entire circumference of the sheath 620. However, for example, in the OCT measurement in the case where the radial scanning needs not be performed over the entire circumference of the sheath 620, such as the case of measurement of the stomach wall, when the configuration as shown in FIG. 15 is used, an optical structure image which requires the radial scanning to be performed in a limited region can be acquired at high speed only by rotating the n-reflecting surface body 621 by 60 degrees (360 degrees×1/n).

That is, in the case where m is an integer of n or more, the m-reflecting surface body 621 may be configured to have a substantially m-sided pyramid shape formed in such a manner that the vertex side of an m-sided pyramid having a planar m-sided polygon shaped bottom surface is cut at a predetermined height from the bottom surface, and may be configured to have m light deflecting surfaces that are formed by the side surfaces of the substantially m-sided pyramid and that are arranged to be rotatable about the longitudinal axis. Note that when the number of channels in fibers 623 is two, the three-reflecting surface body 621 (see FIG. 6) configured by three light deflecting surfaces is used.

In the above, an optical structure measuring apparatus and its optical probe are described in detail, but the present invention is not limited to the above described examples. It is obvious that various modification and changes are possible within the scope and spirit of the invention.

What is claimed is:

1. An optical structure measuring apparatus comprising:
an optical probe having a thin and long sheath whose distal end is closed, an n-channel waveguide device in which n is an integer of three or more and which is inserted and fixed in the sheath along the longitudinal axis of the sheath so as to guide light beams, an irradiating device which is provided in a distal end portion of the sheath and which deflects a light beam emitted from each of the channels of the n-channel waveguide device in a radial direction about the longitudinal axis of the sheath to irradiate a measuring object with the deflected light beam, a rotating device which rotates the irradiating device about the longitudinal axis, and a forward/backward moving device which moves forward and backward the n-channel waveguide device and the irradiating device in the direction along the longitudinal axis;
a light source device which emits a light beam having wavelengths in a wide band;
a branching device which branches the light beam from the light source device to a measuring light beam and a reference light beam;
a branching and light guiding device which branches the measuring light beam to each of the channels of the n-channel waveguide device to allow the branched light beam to be guided by each of the channels of the n-channel waveguide device;
an n-channel interference light detecting device which detects an interference light beam obtained, for each of the channels of the n-channel waveguide device, by making the reference light beam interfere with a return light beam as the measuring light beam which is returned from the measuring object by being guided by each of the channels of the n-channel waveguide device via the branching and light guiding device;
an n-channel interference signal generating device which generates an interference signal representing a signal intensity in the depth direction of the measuring object on the basis of each of the interference light beams detected by the n-channel interference light beam detecting device; and a tomographic structure image generating device which generates a tomographic structure image of the measuring object on the basis of each of the interference signals generated by the n-channel interference signal generating device.

2. The optical structure measuring apparatus according to claim 1, wherein the irradiating device is configured by an n-surface light deflecting and irradiating device which has a substantially n-sided pyramid shape formed in such a manner that a vertex side of an n-sided pyramid having a planar n-sided polygon shaped bottom surface is cut at a predetermined height from the bottom surface, and which has n light deflecting surfaces that are formed by the side surfaces of the substantially n-sided pyramid, and that are arranged to be rotatable about the longitudinal axis.

3. The optical structure measuring apparatus according to claim 2, wherein the planar n-sided polygon shape is formed into a rotationally symmetrical shape about the longitudinal axis.

4. The optical structure measuring apparatus according to claim 1, wherein the rotating device is configured by including:
a torque transmitting coil, a distal end of which is integrally connected to the rotation center of the n-surface light deflecting and irradiating device, and which is rotatably inserted in the sheath along the longitudinal axis of the sheath; and
a motor, a rotary shaft of which is connected to the proximal end of the torque transmitting coil, and which rotates the torque transmitting coil about the longitudinal axis.

5. The optical structure measuring apparatus according to claim 1, wherein the rotating device is configured by a motor which is provided in the sheath on the distal end side from the n-surface light deflecting and irradiating device, and which uses, as its rotary shaft, the longitudinal axis integrally connected to the rotation center of the n-surface light deflecting and irradiating device.

6. The optical structure measuring apparatus according to claim 1, wherein the branching device is configured by an n-channel branching device each channel of which is provided for each of the channels of the n-channel interference light detecting device.

7. The optical structure measuring apparatus according to claim 1, further comprising an n-channel reference light branching device that branches the reference light beam into channel reference light beams each of which corresponds to each of the channels of the n-channel interference light detecting device, and each of which is made to interfere with each return light beam as the measuring light beam that is guided from the measuring object by each of the channels of the n-channel waveguide device via the branching and light guiding device.

8. The optical structure measuring apparatus according to claim 1, further comprising an optical path length correcting device which corrects the optical path length of the reference light beam.

9. The optical structure measuring apparatus according to claim 7, further comprising n or n−1 channel optical path length correcting devices, each of which is provided for each of the channels of the n-channel interference light detecting device, so as to correct the optical path length of the channel reference light beam.

10. The optical structure measuring apparatus according to claim 1, wherein the light source device is configured by n or less light sources each of which emits the light beam having wavelengths in the wide band.

11. The optical structure measuring apparatus according to claim 1, further comprising a three-dimensional structure image generating device which generates a three-dimensional structure image of the measuring object on the basis of a plurality of tomographic structure images taken along the longitudinal axis.

12. An optical structure measuring apparatus comprising:
an optical probe having a thin and long sheath whose distal end is closed, an n-channel waveguide device in which n is an integer of two or more and which is inserted and fixed in the sheath along the longitudinal axis of the sheath so as to guide light beams, an irradiating device which is provided in a distal end portion of the sheath and which deflects a light beam emitted from each of the channels of the n-channel waveguide device in a radial direction about the longitudinal axis of the sheath to irradiate a measuring object with the deflected light beam, a rotating device which rotates the irradiating device about the longitudinal axis, and a forward/backward moving device which moves forward and backward the n-channel waveguide device and the irradiating device in the direction along the longitudinal axis;
a light source device which emits a light beam having wavelengths in a wide band;
a branching device which branches the light beam from the light source device to a measuring light beam and a reference light beam;
a branching and light guiding device which branches the measuring light beam to each of the channels of the n-channel waveguide device to allow the branched light beam to be guided by each of the channels of the n-channel waveguide device;
an n-channel interference light detecting device which detects an interference light beam obtained, for each of the channels of the n-channel waveguide device, by making the reference light beam interfere with a return light beam as the measuring light beam which is returned from the measuring object by being guided by each of the channels of the n-channel waveguide device via the branching and light guiding device;
an n-channel interference signal generating device which generates an interference signal representing a signal intensity in the depth direction of the measuring object on the basis of each of the interference light beams detected by the n-channel interference light beam detecting device; and
a tomographic structure image generating device which generates a tomographic structure image of the measuring object on the basis of each of the interference signals generated by the n-channel interference signal generating device.

13. The optical structure measuring apparatus according to claim 12, wherein when m is an integer of n or more, the irradiating device is configured by an m-surface light deflecting and irradiating device which has a substantially m-sided pyramid shape formed in such a manner that a vertex side of an m-sided pyramid having a planar m-sided polygon shaped bottom surface is cut at a predetermined height from the bottom surface, and which has m light deflecting surfaces that are formed by the side surfaces of the substantially m-sided pyramid, and that are arranged to be rotatable about the longitudinal axis.

14. The optical structure measuring apparatus according to claim 13, wherein when n=2, m is set as m=3.

15. An optical probe of an optical structure measuring apparatus, comprising:
- a thin and long sheath whose distal end is closed;
- an n-channel waveguide device in which n is an integer of three or more and which is inserted and fixed in the sheath along a longitudinal axis of the sheath so as to guide light beams;
- an irradiating device which is provided in a distal end portion of the sheath and which deflects a light beam emitted from each of the channels of the n-channel waveguide device in a radial direction about the longitudinal axis of the sheath to irradiate a measuring object with the deflected light beam;
- a rotating device which rotates the irradiating device about the longitudinal axis; and
- a forward/backward moving device which moves forward and backward the n-channel waveguide device and the irradiating device in the direction along the longitudinal axis.

16. The optical probe of the optical structure measuring apparatus according to claim 15, wherein the irradiating device is configured by an n-surface light deflecting and irradiating device which has a substantially n-sided pyramid shape formed in such a manner that a vertex side of an n-sided pyramid having a planar n-sided polygon shaped bottom surface is cut at a predetermined height from the bottom surface, and which has n light deflecting surfaces that are formed by the side surfaces of the substantially n-sided pyramid, and that are arranged to be rotatable about the longitudinal axis.

17. The optical probe of the optical structure measuring apparatus according to claim 16, wherein the planar n-sided polygon shape is formed into a rotationally symmetrical shape about the longitudinal axis.

18. The optical probe of the optical structure measuring apparatus according to claim 15, wherein the rotating device is configured by including:
- a torque transmitting coil, a distal end of which is integrally connected to the rotation center of the n-surface light deflecting and irradiating device, and which is rotatably inserted in the sheath along the longitudinal axis of the sheath; and
- a motor, a rotary shaft of which is connected to the proximal end of the torque transmitting coil, and which rotates the torque transmitting coil about the longitudinal axis.

19. The optical probe of the optical structure measuring apparatus according to claim 15, wherein the rotating device is configured by a motor which is provided in the sheath on the distal end side from the n-surface light deflecting and irradiating device, and which uses, as its rotary shaft, the longitudinal axis integrally connected to the rotation center of the n-surface light deflecting and irradiating device.

20. An optical probe of an optical structure measuring apparatus, comprising:
- a thin and long sheath whose distal end is closed;
- an n-channel waveguide device in which n is an integer of two or more and which is inserted and fixed in the sheath along a longitudinal axis of the sheath so as to guide light beams;
- an irradiating device which is provided in a distal end portion of the sheath and which deflects a light beam emitted from each of the channels of the n-channel waveguide device in a radial direction about the longitudinal axis of the sheath to irradiate a measuring object with the deflected light beam;
- a rotating device which rotates the irradiating device about the longitudinal axis; and
- a forward/backward moving device which moves forward and backward the n-channel waveguide device and the irradiating device in the direction along the longitudinal axis.

21. The optical probe of the optical structure measuring apparatus according to claim 20, wherein when m is an integer of n or more, the irradiating device is configured by an m-surface light deflecting and irradiating device which has a substantially m-sided pyramid shape formed in such a manner that the vertex side of an m-sided pyramid having a planar m-sided polygon shaped bottom surface is cut at a predetermined height from the bottom surface, and which has m light deflecting surfaces that are formed by the side surfaces of the substantially m-sided pyramid, and that are arranged to be rotatable about the longitudinal axis.

22. The optical probe of the optical structure measuring apparatus according to claim 21, wherein when n=2, m is set as m=3.

* * * * *